US011549079B2

(12) United States Patent
Post et al.

(10) Patent No.: US 11,549,079 B2
(45) Date of Patent: Jan. 10, 2023

(54) ODORANTS AND COMPOSITIONS COMPRISING ODORANTS

(71) Applicant: S H KELKAR & COMPANY LIMITED, Maharashtra (IN)

(72) Inventors: Freddy Post, Arnhem (NL); Leszek Doszczak, Amersfoort (NL); Nitesh Chaudhari, Maharashatra (IN)

(73) Assignee: S H KELKAR & COMPANY LIMITED

( * ) Notice: Subject to any disclaimer, the term of this patent is extended or adjusted under 35 U.S.C. 154(b) by 0 days.

(21) Appl. No.: 16/755,874

(22) PCT Filed: Oct. 16, 2018

(86) PCT No.: PCT/EP2018/078292
§ 371 (c)(1),
(2) Date: Apr. 13, 2020

(87) PCT Pub. No.: WO2019/076926
PCT Pub. Date: Apr. 25, 2019

(65) Prior Publication Data
US 2020/0299611 A1 Sep. 24, 2020

(30) Foreign Application Priority Data

Oct. 17, 2017 (IN) .............................. 201721036891
Dec. 13, 2017 (EP) ...................................... 17206935

(51) Int. Cl.
| | |
|---|---|
| *C11B 9/00* | (2006.01) |
| *A23L 27/20* | (2016.01) |
| *A61L 9/015* | (2006.01) |
| *C07C 249/08* | (2006.01) |
| *C07C 251/40* | (2006.01) |
| *A61L 9/01* | (2006.01) |
| *C07C 45/45* | (2006.01) |

(52) U.S. Cl.
CPC .......... *C11B 9/0007* (2013.01); *A23L 27/203* (2016.08); *A23L 27/204* (2016.08); *A23L 27/2024* (2016.08); *A23L 27/2026* (2016.08); *A61L 9/01* (2013.01); *A61L 9/015* (2013.01); *C07C 45/45* (2013.01); *C07C 249/08* (2013.01); *C07C 251/40* (2013.01); *C11B 9/0015* (2013.01); *C11B 9/0061* (2013.01); *A23V 2002/00* (2013.01); *C07C 2601/02* (2017.05); *C07C 2601/04* (2017.05); *C07C 2601/08* (2017.05); *C07C 2601/14* (2017.05); *C07C 2601/16* (2017.05)

(58) Field of Classification Search
CPC . A23V 2002/00; A23L 27/204; A23L 27/203; A23L 27/2026; C11B 9/0015; C11B 9/0007; C07C 251/40; C07C 249/08
See application file for complete search history.

(56) References Cited

U.S. PATENT DOCUMENTS

| | | | | |
|---|---|---|---|---|
| 4,544,714 A | * | 10/1985 | Ochsner ................ | C11B 9/0007 131/276 |
| 5,066,641 A | | 11/1991 | Narula et al. | |
| 2004/0138092 A1 | | 7/2004 | Markert et al. | |

FOREIGN PATENT DOCUMENTS

| | | |
|---|---|---|
| EP | 0071248 A1 | 2/1983 |
| EP | 0085352 A2 | 8/1983 |
| EP | 0191365 A1 | 8/1986 |
| WO | WO01/00551 A1 | 1/2001 |
| WO | WO0112574 A1 | 2/2001 |

OTHER PUBLICATIONS

International Search Report and Written Opinion for PCT/EP2018/078292 dated Jan. 18, 2019.
Vatsadze S. Z., et al.: "Stereocontrol in Preparation of Cyclopalladated Alkylaromatic Oximes and Evaluation of Their Stereoselective Esterase-Type Catalytic Activity", Organometallics, vol. 36, Aug. 18, 2017 (Aug. 18, 2017), pp. 3068-3075.
Ramos et al: "Functionalisation of terpenoids at C-4 via organopalladium dimers: cyclopropane formation during oxidation of homoallylic @s-organopalladium intermediates with lead tetraacetate", Tetrahedron, Elsevier Science Publishers, Amsterdam, NL, vol. 63, No. 51, Nov. 8, 2007 (Nov. 8, 2007), pp. 12608-12615, XP022336711, ISSN: 0040-4020, DOI: 10.1016/J.TET.2007.10.016.
Database DAtabase PubChem Compound [Online] National Center for Biotechnology Information; Dec. 18, 2015 (Dec. 18, 2015), "1,2,2,3,3-Pentamethyl-I-propanone", XP002778669, retrieved from NCBI Database accession No. CID.101613776.
Mouhib Halima et al: "From cats and blackcurrants: structure and dynamics of the sulfur-containing cassis odorant cat ketone.", Chemistry & Biodiversity Oct. 2014, vol. 11, No. 10, Oct. 2014 (Oct. 2014), pp. 1554-1566, XP002778670, ISSN: 1612-1880.
Database Registry [Online] Chemical Abstracts Service, Columbus, Ohio, US; Aug. 24, 2005 (Aug. 24, 2005), "1-Butanone, 2,2,3-trimethy1-1-phenyl-, oxime", Database accession No. 861534-83-0.

* cited by examiner

*Primary Examiner* — Genevieve S Alley
(74) *Attorney, Agent, or Firm* — Maschoff Brennan

(57) ABSTRACT

The present invention relates to new classes of odorous oximes and their ketone intermediates (odorants) which are useful as fragrance or flavor materials in particular in providing cassis, catty, tropical, green, coniferous, thuya, floral and/or fruity olfactory notes to perfume, aroma or deodorizing/masking compositions.

20 Claims, 2 Drawing Sheets

ODORANTS AND COMPOSITIONS COMPRISING ODORANTS

FIELD OF THE INVENTION

The present invention relates to new classes of odorous oximes which are useful as fragrance or flavor materials in particular in providing cassis, catty, tropical and/or green olfactory notes and the corresponding odorous ketones (intermediates) also useful as fragrance or flavor materials in particular in providing coniferous, thuya, floral and/or fruity notes to perfume, aroma or deodorizing/masking compositions and also conferring to said compositions one or more of the following advantages/properties: lack of sulfury off-notes, complex odor profile, natural impression, high volatility (influencing top notes), and/or solubility. The present invention also relates to fragrance, flavor and/or deodorizing/masking compositions comprising said new classes of odorant oximes and the corresponding parent ketones (intermediates). The present invention furthermore refers to the said odorants which can be used in the novel fragrance, flavor and/or deodorizing/masking compositions of the present invention. The present invention also refers to a method for the production of the said odorants/compounds and of the corresponding fragrance, flavor and/or deodorizing/masking compositions containing said odorants/compounds.

BACKGROUND OF THE INVENTION

Typically, many odorants that are presently utilized in the perfumery industry and/or the flavor industry are synthetic molecules. In particular, there is a high demand and need for novel odorants/compounds and/or for novel fragrance, flavor and/or deodorizing/masking compositions comprising said odorants/compounds.

For industrial applications it is beneficial if various products can be derived from one basic scaffold/raw material. It becomes even more beneficial if the raw material is exclusive in certain aspects. 2,3-Dimethylbutenes 1 and 2 are almost exclusively used for production of substituted tetralines (3) and in particular in production of Tonalid (4).

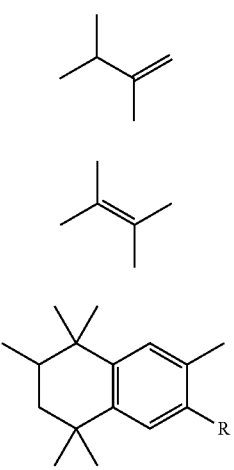

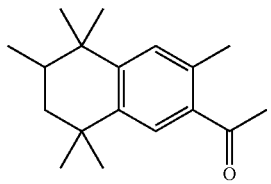

Therefore, in the course of their research and development activities, the Applicants started to develop products based on 2,3-dimethylbutenes 1 and 2 as a raw material(s) for novel odorants. It is an advantage of one or more of the embodiments of the present invention that the claimed odorants/compounds derived from 2,3-dimethylbutenes can impart and/or accentuate particular olfactory notes, in particular providing cassis, catty, tropical, green, coniferous, thuya, floral, and/or fruity olfactory notes to fragrance, flavor and/or deodorizing/masking compositions, and also confer to said compositions one or more of the following advantages/properties: lack of sulfury off-notes, complex odor profile, natural impression, high volatility (influencing top notes), and/or solubility.

PRIOR ART

The article entitled "Functionalisation of terpenoids at C-4 via organopalladium dimers: cyclopropane formation during oxidation of homoallylic σ-organopalladium intermediates with lead tetraacetate", referenced as https://doi.org/10.1016/j.tet.2007.10.016 (Tetrahedron, Volume 63, Issue 51, 17 Dec. 2007, Pages 12608-12615), relates to the synthesis of new potential adjuvant saponin aglycons by selective palladium mediated C—H functionalisation of appropriately functionalised derivatives of lanosterol, cholesterol, and friedelin. In this article, the desired equatorial aldehyde functionality was successfully introduced into the lanosterol skeleton as expected; the cyclopalladation of a cholesterol derivative proceeded as expected; however, during oxidation of the organopalladium intermediate, participation of the adjacent alkene functionality led to stereoselective formation of a cyclopropane and introduction of an acetate group into the steroid backbone at C-6. In order to further explore this unusual cyclopropane formation during the oxidation of the organopalladium intermediate, the authors prepared 3,3,4-trimethylpent-4-en-2-one oxime (compound 23 in said article) by $ZnCl_2$ mediated acylation of tetramethylethylene and subsequent treatment of the thus formed 3,3,4-trimethylpent-4-en-2-one with hydroxylamine. Said oxime 23, which corresponds to our 3,3,4-trimethylpent-4-en-2-one oxime of Example 2 herein below, is then treated with $Na_2PdCl_4$ to form a yellow precipitate as for the other systems, but without insertion into any of the methyl C—H bonds. Said compound 23 is an intermediate compound which is used during an investigation of the unusual cyclopropane formation faced by Ramos et al. in this article which is far remote from having any fragrance related application consideration.

Compound 1,2,2,3,3-Pentamethyl-1-propanone is cited in Database PubChem [Online] from the National Center for Biotechnology Information; 18 Dec. 2015. There is no mention at all of the potential olfactory property of this compound.

SUMMARY OF THE INVENTION

This invention discloses novel fragrance, flavor and/or deodorizing/masking compositions comprising an oxime selected from compounds of formula (7) or of formula (8)

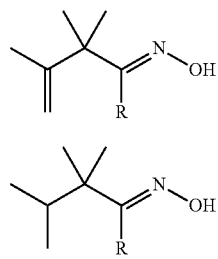

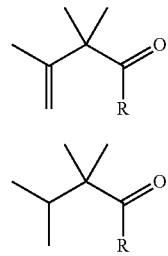

wherein R is an alkyl group having from 1 to 9 carbon atoms, an alkenyl group containing only one carbon-carbon double bond (said carbon-carbon double bond being preferably not conjugated with the oxime C═N bond) and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment according to the present invention, R is methyl, ethyl, n-propyl, propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 3-butenyl, 5-(2-methylpent-2-en)yl, 4-pent-2-enyl, 4-pent-1-enyl, 5-(2,5-dimethylhex-2-en)yl, benzyl, phenyl, or 4-methoxyphenyl.

In another embodiment the compounds of this invention can occur as stereoisomers e.g. as compounds with Z and E configuration of the C═N bond or as a mixture of thereof.

In another embodiment when R group contains chiral centers, the compounds of this invention can occur as stereoisomers e.g. as compounds with R or S configuration or as a mixture of thereof.

In another embodiment when R is an alkenyl group containing only one carbon-carbon double bond (said carbon-carbon double bond being preferably not conjugated with the oxime C═N bond) and having up to 9 carbon atoms, the compounds of this invention can occur as stereoisomers e.g. as compounds with Z or E configuration of the C═C bond or as a mixture of thereof.

In another embodiment the compounds of this invention can be chiral, e.g. they can occur as stereoisomeric mixtures, more specifically as mixture of enantiomers; R isomer, S isomer, a racemic mixture and/or a non-racemic mixture of R and S isomers and they can also be advantageously used in pure form or as mixtures.

DETAILED DESCRIPTION

Figure 1:
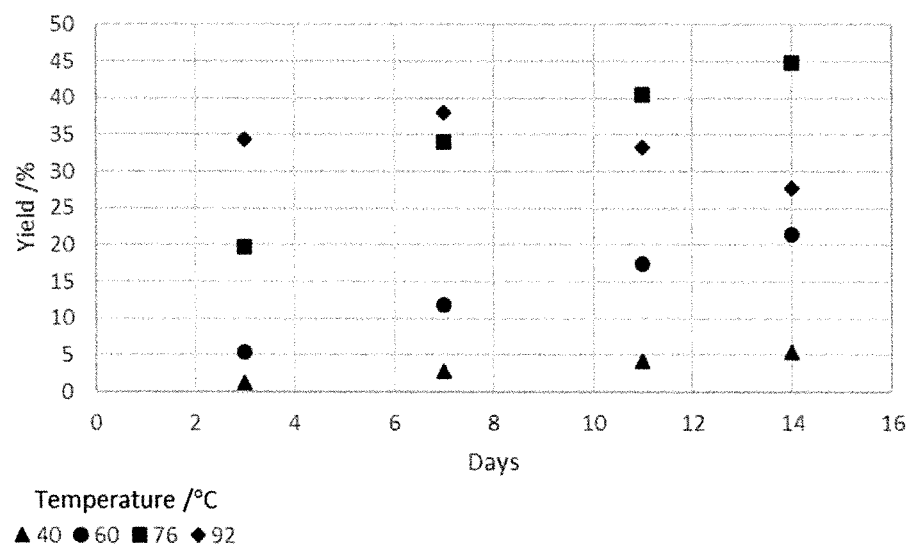
FIG. 1 is a graphic representation of the oxime GC yield vs time.

The term "odorant" characterizing the compounds according to the present invention means that in humans it triggers an odor sensation which is preferably pleasant; it is therefore conventionally used for perfuming industrial and sanitary articles, washing agents, cleaning agents, personal hygiene products, cosmetics and the like. For the purposes of the present invention and appended claims, the term "odorant" includes "aroma substances". Aroma substances is the term usually used to designate substances which provide odor and/or flavor to foodstuffs.

The oxime compounds of formula (7) or of formula (8) may be used alone, as mixtures thereof, or in combination with a base material.

As explained and detailed hereunder, the intermediate ketone compounds of formula (5) or of formula (6) may also be used alone, as mixtures thereof, or in combination with a base material.

As used herein, the "base material" includes all known fragrance/flavor materials selected from the extensive range of natural products like: essential oils, extracts, resinoids or isolates and synthetic materials currently available, such as: hydrocarbons, alcohols, aldehydes and ketones, ethers and acetals, esters and lactones, nitriles, oximes or heterocycles, and/or in admixture with one or more ingredients or excipients/adjuvants conventionally used in conjunction with odorants in fragrance and/or flavor compositions, for example: solvents/diluents, stabilizers, carrier materials, and other auxiliary agents commonly used in the art.

The oxime compounds according to formula (7) or to formula (8)—and/or the ketone compounds of formula (5) or of formula (6)—may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients.

According to a preferred embodiment of the invention, the fragrance, flavor and/or deodorizing/masking composition according to the present invention contains at least one oxime compound according to formula (7) or formula (8) as previously described and/or at least one ketone compound of formula (5) or of formula (6) as further described herein below, in quantities between 0.00001 and 99.9 wt. %, for example between 0.0001 and 95 wt. %, for example between 0.001 and 25 wt. %, preferably between 0.01 and 15 wt. %, more advantageously between 0.1 and 10 wt. %, in particular between 1 and 5 wt. %, in each case relative to the entire composition. In a particular embodiment of the invention, the fragrance, flavor and/or deodorizing/masking composition according to the present invention contains mixture of at least one oxime compound of formula (7) and at least one corresponding ketone compound of formula (5) [i.e. the ketone having the same radical R]. In a particular embodiment of the invention, the fragrance, flavor and/or deodorizing/masking composition according to the present invention contains mixture of at least one oxime compound of formula (8) and at least one corresponding ketone compound of formula (6) [i.e. the ketone having the same radical R].

The use of more than one oxime compound according to formula (7) or formula (8) in a fragrance, flavor and/or deodorizing/masking composition according to the present invention can be particularly advantageous when the difference of the number of carbon atoms of the respective oximes of the same generic formula is between 1 and 9, for example between 1 and 5, preferably between 1 and 4, more advantageously between 1 and 3, in particular between 1 and 2. When a mixture of oximes is used, the weight ratio between the oxime present in highest weight and the oxime present in the second highest weight in the mixture is comprised between 99.9% and 50% for example between 99% and 70%, preferably between 98% and 80%, more advantageously between 98% and 90%, in particular between 98% and 95%.

The use of more than one ketone compound according to formula (5) or formula (6) in a fragrance, flavor and/or deodorizing/masking composition according to the present invention can be particularly advantageous when the difference of the number of carbon atoms of the respective ketone of the same generic formula is between 1 and 9, for example between 1 and 5, preferably between 1 and 4, more advantageously between 1 and 3, in particular between 1 and 2. When a mixture of ketones is used, the weight ratio between the ketone present in highest weight and the ketone present in the second highest weight in the mixture is comprised between 99.9% and 50% for example between 99% and 70%, preferably between 98% and 80%, more advantageously between 98% and 90%, in particular between 98% and 95%.

According to a particularly preferred embodiment of the invention, in addition to the compound of formula (7) or of formula (8) and/or the compound of formula (5) or of formula (6) according to the present invention, the fragrance, flavor and/or deodorizing/masking composition according to the present invention contains additional odorants, for example in a quantity of 0.1 to 99.9 wt. %, preferably 5-90 wt. %, in particular 15-70 wt. %, relative to the entire fragrance and/or flavor composition.

The compounds of formula (7) or of formula (8) as described hereinabove and/or the compounds of formula (5) or of formula (6) as described hereafter may be employed in a consumer product base simply by directly mixing at least one compound of formula (7) or of formula (8) and/or at least one compound of formula (5) or of formula (6), or a fragrance composition comprising said compound of formula (7) or of formula (8) and/or said compound of formula (5) or of formula (6) with the consumer product base; or they may, in an earlier step, be entrapped with an entrapment material, for example, polymers, capsules, microcapsules and/or nanocapsules, liposomes, film formers, absorbents such as active carbon or zeolites, cyclic oligosaccharides, cyclic glycourils, and mixtures of two or more thereof, or they may be chemically bonded to substrates, which are adapted to release the fragrance molecule upon application of an external stimulus such as light, enzyme, air, water or the like, and then mixed with the consumer product base.

Thus, the invention can be useful for existing methods of manufacturing a fragrance, flavor and/or deodorizing/masking composition, comprising the incorporation of a compound of formula (7) or of formula (8) and/or of a compound of formula (5) or of formula (6), as a fragrance, flavor and/or deodorizing/making ingredient, either by directly admixing the compound to the consumer product base or by admixing a fragrance, flavor and/or deodorizing/masking composition comprising said compound of formula (7) or of formula (8) and/or said compound of formula (5) or of formula (6), which may then be mixed with a consumer product base, using conventional techniques and methods. Through the addition of an olfactory-acceptable amount of at least one compound of formula (7) or of formula (8) and/or at least one compound of formula (5) or of formula (6) of the present invention as hereinabove/hereafter described, the odor notes of a consumer product base can be improved, enhanced, and/or modified.

The present invention provides fragrance, flavor and/or deodorizing/masking compositions comprising an oxime selected from compounds of formula (7) or of formula (8)

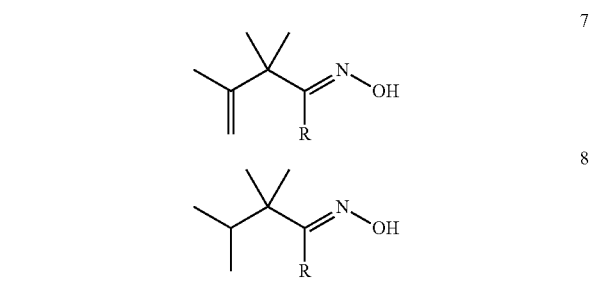

wherein R is an alkyl group having from 1 to 9 carbon atoms, an alkenyl group containing only one carbon-carbon double bond (said carbon-carbon double bond being preferably not conjugated with the oxime C═N bond) and having up to 9 carbon atoms, a (substituted) aryl group having up to 8 carbon atoms, an oxo-alkyl group having up to 9 carbon atoms, or an alkoxyaryl group containing up to 9 carbon atoms or (substituted) benzyl group having up to 9 carbon atoms.

In an embodiment according to the present invention, R is methyl, ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 3-butenyl, 5-(2-methylpent-2-en)yl, 4-pent-2-enyl, 4-pent-1-enyl, 5-(2,5-dimethylhex-2-en)yl, benzyl, phenyl, or 4-methoxyphenyl.

In an embodiment according to the present invention, the fragrance, flavor and/or deodorizing/masking composition comprises the compound of formula (7) or of formula (8) which is selected from

| Structure | Chemical name |
|---|---|
| 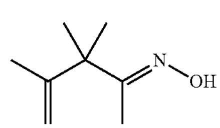 | 3,3,4-trimethylpent-4-en-2-one oxime |

-continued

| Structure | Chemical name |
|---|---|
| 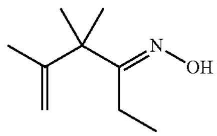 | 4,4,5-trimethylhex-5-en-3-one oxime |
| 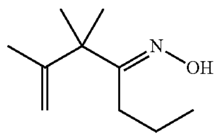 | 2,3,3-trimethylhept-1-en-4-one oxime |
| 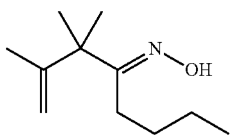 | 2,3,3-trimethyloct-1-en-4-one oxime |
| 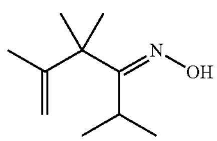 | 2,4,4,5-tetramethylhex-5-en-3-one oxime |
| 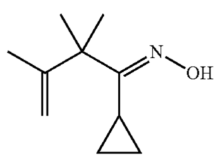 | 1-cyclopropyl-2,2,3-trimethylbut-3-en-one oxime |
| 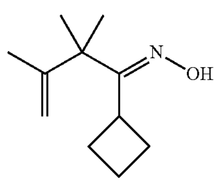 | 1-cyclobutyl-2,2,3-trimethylbut-3-en-1-one oxime |
| 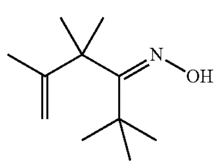 | 2,2,4,4,5-pentamethylhex-5-en-3-one oxime |
| 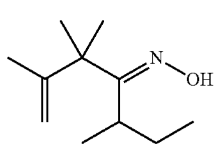 | 2,3,3,5-tetramethylhept-1-en-4-one oxime |
| 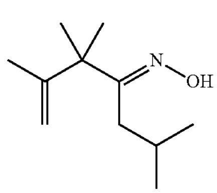 | 2,3,3,6-tetramethylhept-1-en-4-one oxime |

-continued

| Structure | Chemical name |
|---|---|
| 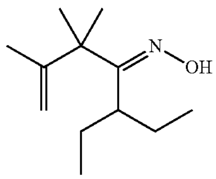 | 5-ethyl-2,3,3-trimethylhept-1-en-4-one oxime |
| 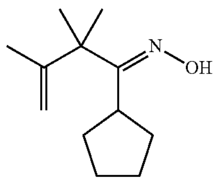 | 1-cyclopentyl-2,2,3-trimethylbut-3-en-1-one oxime |
| 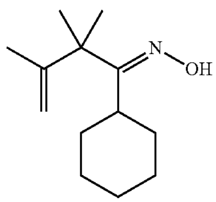 | 1-cyclohexyl-2,2,3-trimethylbut-3-en-1-one oxime |
| 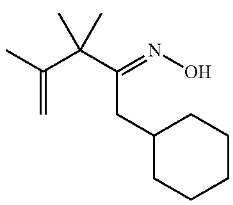 [SMILES: C=C(C)C(C)(C)/C(CC1CCCCC1)=N/O] | 1-cyclohexyl-3,3,4-trimethylpent-4-en-2-one oxime |
| 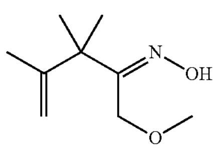 | 1-methoxy-3,3,4-trimethylpent-4-en-2-one oxime |
| 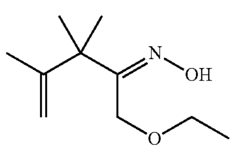 | 1-ethoxy-3,3,4-trimethylpent-4-en-2-one oxime |
| 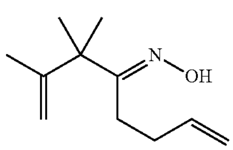 | 2,3,3-trimethylocta-1,7-dien-4-one oxime |
| 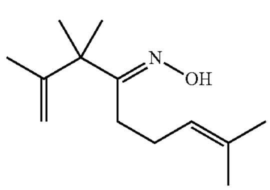 | 2,3,3,8-tetramethylnona-1,7-dien-4-one oxime |
| 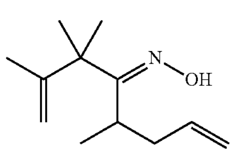 | 2,3,3,5-tetramethylocta-1,7-dien-4-one oxime |

-continued

| Structure | Chemical name |
|---|---|
| 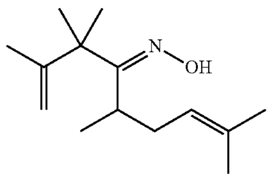 [SMILES: C=C(C)C(C)(C)/C(=N/O)C(C)CC=C(C)C] | 2,3,3,5,8-pentamethylnona-1,7-dien-4-one oxime |
| 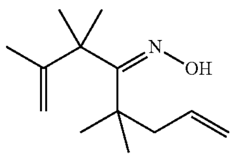 | 2,3,3,5,5-pentamethylocta-1,7-dien-4-one oxime |
| 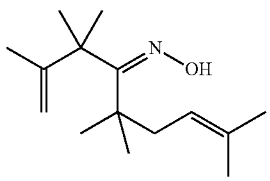 [SMILES: C=C(C)C(C)(C)/C(=N/O)C(C)(C)CC=C(C)C] | 2,3,3,5,5,8-hexamethylnona-1,7-dien-4-one oxime |
| 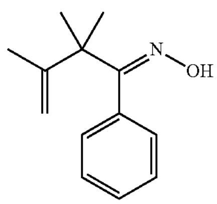 | 2,2,3-trimethyl-1-phenylbut-3-en-1-one oxime |
| 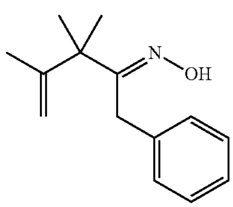 [SMILES: C=C(C)C(C)(C)/C(Cc1ccccc1)=N/O] | 3,3,4-trimethyl-1-phenylpent-4-en-2-one oxime |
| 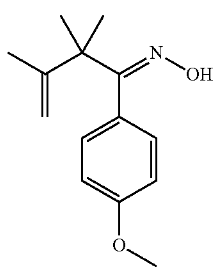 [SMILES: C=C(C)C(C)(C)/C(=N/O)c1ccc(OC)cc1] | 1-(4-methoxyphenyl)-2,2,3-trimethylbut-3-en-1-one oxime |
| 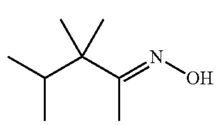 | 3,3,4-trimethylpentan-2-one oxime |
| 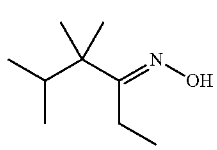 | 4,4,5-trimethylhexan-3-one oxime |

-continued

| Structure | Chemical name |
|---|---|
| 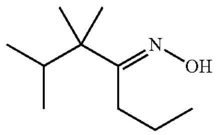 | 2,3,3-trimethylheptan-4-one oxime |
| 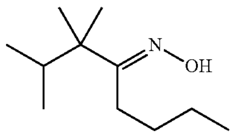 | 2,3,3-trimethyloctan-4-one oxime |
| 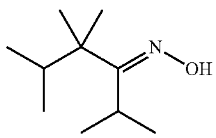 | 2,4,4,5-tetramethylhexan-3-one oxime |
| 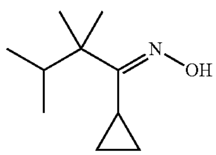 | 1-cyclopropyl-2,2,3-trimethylbutan-1-one oxime |
| 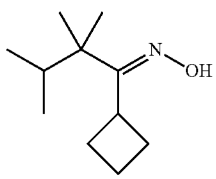 | 1-cyclobutyl-2,2,3-trimethylbutat-1-one oxime |
| 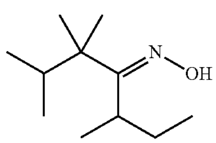 | 2,3,3,5-tetramethylheptan-4-one oxime |
| 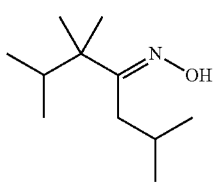 | 2,3,3,6-tetramethylheptan-4-one oxime |
| 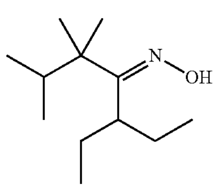 | 5-ethyl-2,3,3-trimethylheptan-4-one oxime |
| 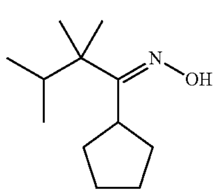 | 1-cyclopentyl-2,2,3-trimethylbutan-1-one oxime |

-continued

| Structure | Chemical name |
|---|---|
| 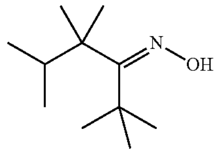 | 2,2,4,4,5-pentamethylhexan-3-one oxime |
| 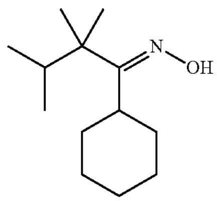 | 1-cyclohexyl-2,2,3- trimethylbutan-1-one oxime |
| 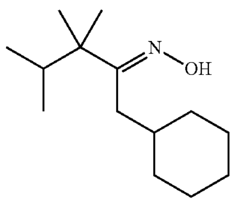 | 1-cyclohexyl-3,3,4-trimethylpentan-2-one oxime |
| 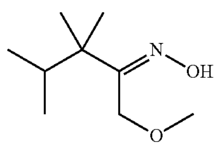 | 1-methoxy-3,3,4-trimethylpentan-2-one oxime |
| 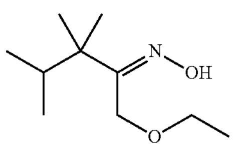 | 1-ethoxy-3,3,4-trimethylpentan-2-one oxime |
| 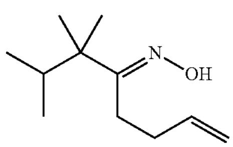 | 2,2,3-trimethyloct-7-en-4-one oxime |
| 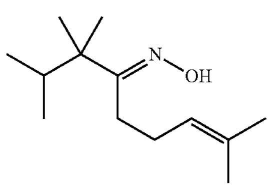 | 2,3,3,8-tetramethylnon-7-en-4-one oxime |
| 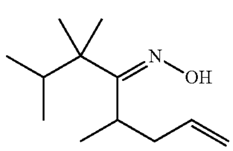 | 2,3,35-tetramethyloct-7-en-4-one oxime |
| 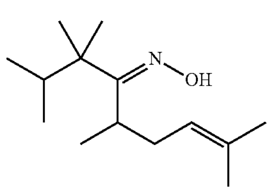 [SMILES: CC(C)=CCC(C)/C(=N\O)C(C)(C)C(C)C] | 2,3,3,5,8-pentamethylnon-7-en-4-one oxime |

| Structure | Chemical name |
|---|---|
| 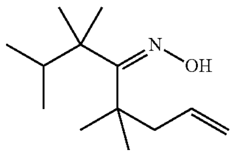 | 2,3,3,5,5-pentamethyloct-7-en-4-one oxime |
| 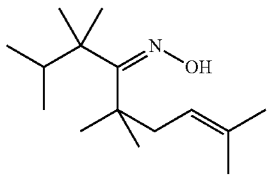 [SMILES: CC(C)=CCC(C)(C)/C(=N\O)C(C)(C)C(C)C] | 2,3,3,5,5,8-hexamethylnon-7-en-4-one oxime |
| 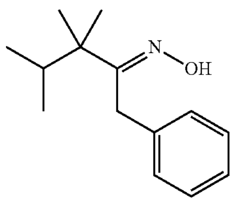 [SMILES: CC(C)C(C)(C)/C(Cc1ccccc1)=N/O] | 3,3,4-trimethyl-1-phenylpentan-2-one oxime |
| 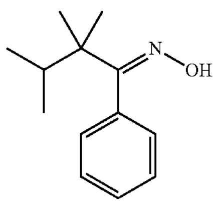 | 2,2,3-trimethyl-1-phenylbutan-1-one oxime |
| | 1-(4-methoxyphenyl)-2,2,3-trimethylbutan-1-one oxime | and/or a mixture of two or more of the said compounds.

The Applicants have also discovered that, from an olfactory perspective, the compounds of formula (7) or of formula (8) have a distinctly cassis, catty, tropical and/or green, profile that lends itself directly to use in fruity compositions such as for example black currant, grapefruit, peach, strawberry, grape and/or passion fruit. Indeed, the compounds of formula (7) or of formula (8) exhibit cassis type note and green isobutyl thiazole like note without sulfury off-notes. It is also more versatile, with easily recognizable applications toward tomato leaf, basil, sage, and/or mint herbs as well as notes like for instance citrus, lily of the valley, and/or sea breeze. Furthermore, compared to other odorants like e.g. corps cassis, the compounds of formula (7) or of formula (8) have greater diffusivity and presence together without sulfury off-notes which makes it very valuable. They have greater stability and volatility in various application media in particular basic media.

For example, when R is selected as propyl, isopropyl, and/or sec-butyl in the compounds of formula (7) or of formula (8), the Applicants have discovered that a very diffusive, green, cassis, catty, and/or peachy profile oriented olfactive note could be obtained.

Oximes

In an embodiment, the present invention also provides new compounds of formula (7) useful in the perfume, aroma and/or deodorizing/masking compositions of the present invention

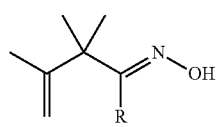

7 wherein R is an alkyl group having from 2 to 9 carbon atoms, an alkenyl group containing only one carbon-carbon double bond (said carbon-carbon double bond being preferably not conjugated with the oxime C=N bond) and having up to 9 carbon atoms, a phenyl group, a substituted aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment according to the present invention, R is ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 3-butenyl, 5-(2-methylpent-2-en)yl, 4-pent-2-enyl, 4-pent-1-enyl, 5-(2,5-dimethylhex-2-en)yl, benzyl, phenyl, or 4-methoxyphenyl.

In an embodiment, the present invention also provides new compounds of formula (8) useful in the perfume, aroma and/or deodorizing/masking compositions of the present invention.

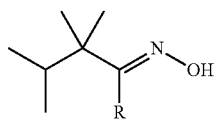

8 wherein R is an alkyl group having from 2 to 9 carbon atoms, an alkenyl group containing only one carbon-carbon double bond and having up to 9 carbon atoms, a substituted aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment according to the present invention, R is ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 3-butenyl, 5-(2-methylpent-2-en)yl, 4-pent-2-enyl, 4-pent-1-enyl, 5-(2,5-dimethylhex-2-en)yl, benzyl, or 4-methoxyphenyl.

In an embodiment according to the present invention, the new compound of formula (7) and/or of formula (8) useful in the perfume, aroma and/or deodorizing/masking compositions of the present invention are selected from

| Structure | Chemical name |
| --- | --- |
|  | 4,4,5-trimethylhex-5-en-3-one oxime |
|  | 2,3,3-trimethylhept-1-en-4-one oxime |
|  | 2,3,3-trimethyloct-1-en-4-one oxime |
|  | 2,4,4,5-tetramethylhex-5-en-3-one oxime |
| 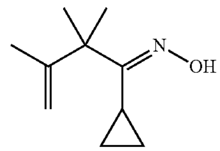 | 1-cyclopropyl-2,2,3-trimethylbut-3-en-1-one oxime |
| 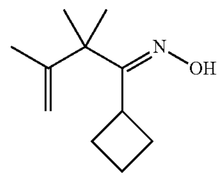 | 1-cyclobutyl-2,2,3-trimethylbut-3-en-1-one oxime |
| 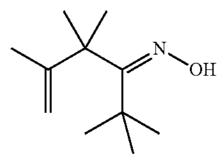 | 2,2,4,4,5-pentamethylhex-5-en-3-one oxime |
| 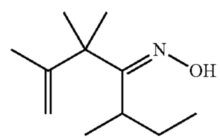 | 2,3,3,5-tetramethylhept-1-en-4-one oxime |
| 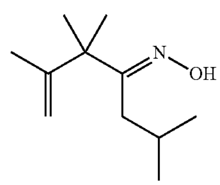 | 2,3,3,6-tetramethylhept-1-en-4-one oxime |
| 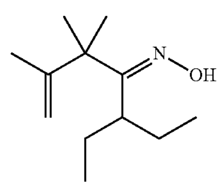 | 5-ethyl-2,3,3-trimethylhept-1-en-4-one oxime |
| 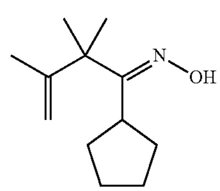 | 1-cyclopentyl-2,2,3-trimethylbut-3-en-1-one oxime |
| 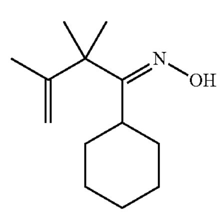 | 1-cyclohexyl-2,2,3-trimethylbut-3-en-1-one oxime |

| Structure | Chemical name |
|---|---|
| 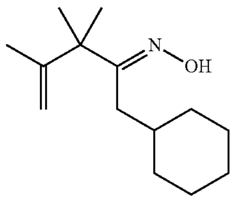 [SMILES: C=C(C)C(C)(C)/C(CC1CCCCC1)=N/O] | 1-cyclohexyl-3,3,4-trimethylpent-4-en-2-one oxime |
| 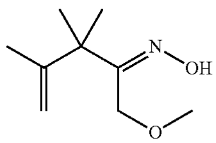 | 1-methoxy-3,3,4-trimethylpent-4-en-2-one oxime |
| 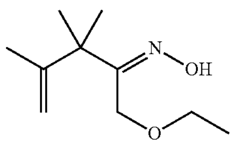 | 1-ethoxy-3,3,4-trimethylpent-4-en-2-one oxime |
| 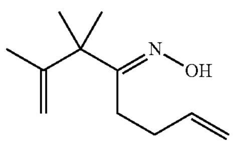 | 2,3,3-trimethylocta-1,7-dien-4-one oxime |
| 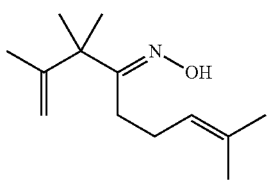 | 2,3,3,8-tetramethylnona-1,7-dien-4-one oxime |
| 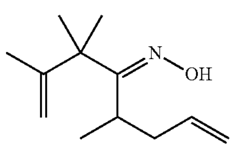 | 2,3,3,5-tetramethylocta-1,7-dien-4-one oxime |
| 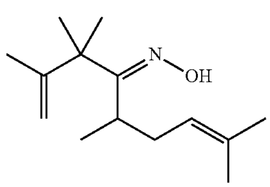 [SMILES: C=C(C)C(C)(C)/C(=N/O)C(C)CC=C(C)C] | 2,3,3,5,8-pentamethylnona-1,7-dien-4-one oxime |
| 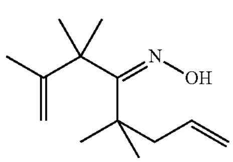 | 2,3,3,5,5-pentamethylocta-1,7-dien-4-one oxime |
| 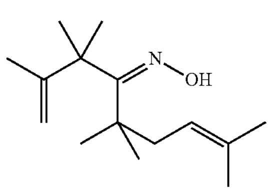 [SMILES: C=C(C)C(C)(C)/C(=N/O)C(C)(C)CC=C(C)C] | 2,3,3,5,5,8-hexamethylnona-1,7-dien-4-one oxime |

| Structure | Chemical name |
|---|---|
| 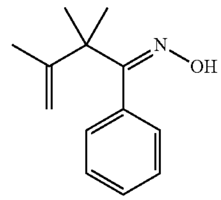 | 2,2,3-trimethyl-1-phenylbut-3-en-1-one oxime |
| 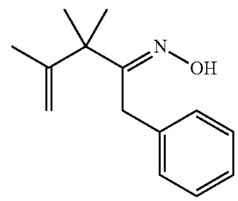 [SMILES: C=C(C)C(C)(C)/C(Cc1ccccc1)=N/O] | 3,3,4-trimethyl-1-phenylpent-4-en-2-one oxime |
| 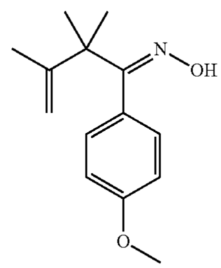 [SMILES: C=C(C)C(C)(C)/C(=N/O)c1ccc(OC)cc1] | 1-(4-methoxyphenyl)-2,2,3-trimethylbut-3-en-1-one oxime |
| 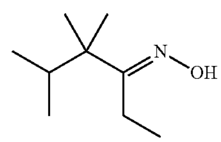 | 4,4,5-trimethylhexan-3-one oxime |
| 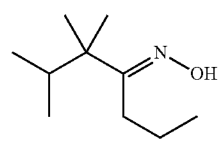 | 2,3,3-trimethylheptan-4-one oxime |
| 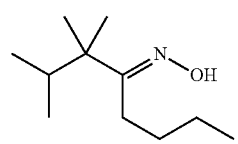 | 2,3,3-trimethyloctan-4-one oxime |
| 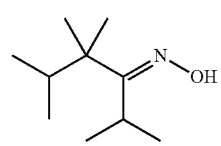 | 2,4,4,5-tetramethylhexan-3-one oxime |
| 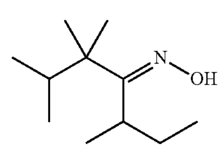 | 2,3,3,5-tetramethylheptan-4-one oxime |
| 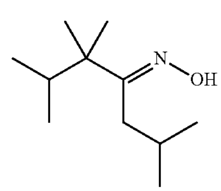 | 2,3,3,6-tetramethylheptan-4-one oxime |

| Structure | Chemical name |
|---|---|
| 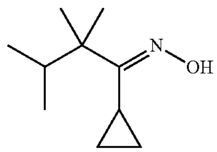 | 1-cyclopropyl-2,2,3-trimethylbutan-1-one oxime |
| 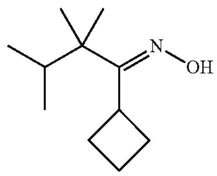 | 1-cyclobutyl-2,2,3-trimethylbutan-1-one oxime |
| 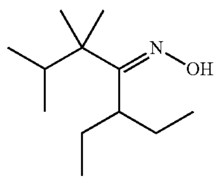 | 5-ethyl-2,3,3-trimethylheptan-4-one oxime |
| 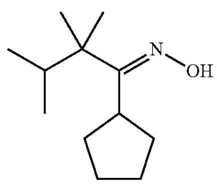 | 1-cyclopentyl-2,2,3-trimethylbutan-1-one oxime |
| 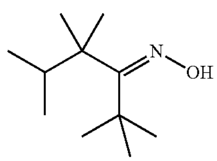 | 2,2,4,4,5-pentamethylhexan-3-one oxime |
| 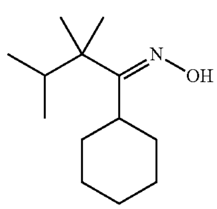 | 1-cyclohexyl-2,2,3-trimethylbutan-1-one oxime |
| 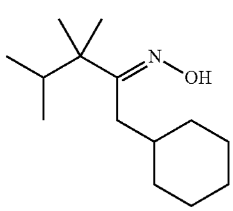 [SMILES: CC(C)C(C)(C)/C(CC1CCCCC1)=N/O] | 1-cyclohexyl-3,3,4-trimethylpentan-2-one oxime |
| 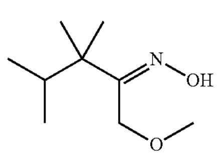 | 1-methoxy-3,3,4-trimethylpentan-2-one oxime |

| Structure | Chemical name |
|---|---|
| 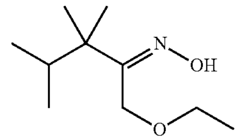 | 1-ethoxy-3,3,4-trimethylpentan-2-one oxime |
| 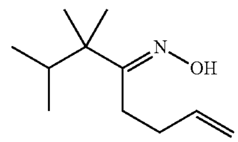 | 2,3,3-trimethyloct-7-en-4-one oxime |
| 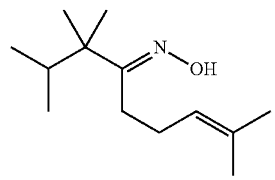 | 2,3,3,8-tetramethylnon-7-en-4-one oxime |
| 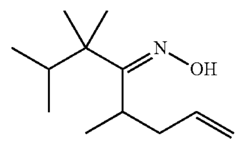 | 2,3,3,5-tetramethyloct-7-en-4-one oxime |
| 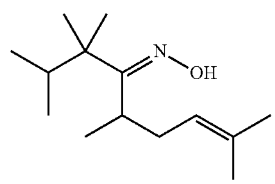 [SMILES: CC(C)=CCC(C)/C(=N\O)C(C)(C)C(C)C] | 2,3,3,5,8-pentamethylnon-7-en-4-one oxime |
| 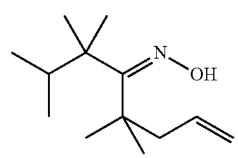 | 2,3,3,5,5-pentamethyloct-7-en-4-one oxime |
| 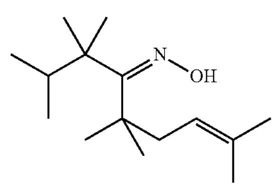 [SMILES: CC(C)=CCC(C)(C)/C(=N\O)C(C)(C)C(C)C] | 2,3,3,5,5,8-hexamethylnon-7-en-4-one oxime |
| 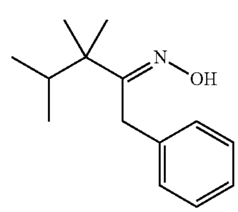 [SMILES: CC(C)C(C)(C)/C(Cc1ccccc1)=N/O] | 3,3,4-trimethyl-1-phenylpentan-2-one oxime |

| Structure | Chemical name | |
|---|---|---|
| 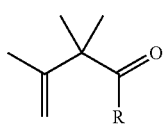 | 1-(4-methoxyphenyl)-2,2,3-trimethylbutan-1-one oxime | 5 | and/or a mixture of two or more of the said compounds.

Preparation

In a preferred embodiment according to the present invention, the compounds of formula (7) and/or of formula (8) can advantageously be prepared from 2,3-dimethylbutene(s) as illustrated hereafter.

Oximation

In an embodiment, the compounds of formula (7) can advantageously be prepared from compounds of formula (5)

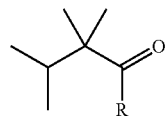

5 wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms, by using an oximation synthesis step, e.g. by reacting the said compounds of formula (5) with hydroxylamine, hydroxylamine in the presence of an acid or a base, a hydroxylamine salt (e.g. hydroxylamine hydrochloride, etc.) in the presence of a base (e.g. sodium acetate, sodium carbonate, potassium hydroxide, ammonium acetate, pyridine, triethyl amine etc.), another oxime in the presence of an acid (e.g. sulphuric acid, perchloric acid, triflic acid etc.) or a base (e.g. potassium hydroxide, pyridine, triethylamine etc.), or a masked hydroxylamine (e.g. N,O-bis(trimethylsilyl)hydroxylamine) in the presence of a strong base (e.g. potassium hydride, potassium bis(trimethylsilyl)amide etc.) to form the compounds of formula (7). In an alternative embodiment, an intermediate alkylation or aldol condensation synthesis step can be performed on the compounds of formula (5) before the oximation step.

In an embodiment, the compounds of formula (8) can advantageously be prepared either from the compounds of formula (7) by using a hydrogenation synthesis step, e.g. by reacting the said compounds of formula (7) with hydrogen (preferably in the presence of a catalyst) to form the compounds of formula (8), or from the compounds of formula (5) as defined hereinabove by using a hydrogenation synthesis step followed by an oximation synthesis step, e.g. by reacting the said compounds of formula (5) with hydrogen (preferably in the presence of a catalyst) to form the compounds of formula (6)

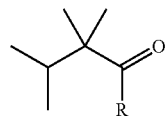

6 wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms, and by reacting the said compounds of formula (6) with hydroxylamine in the presence of an acid, a hydroxylamine salt (e.g. hydroxylamine hydrochloride, etc.) in the presence of a base (e.g. sodium acetate, sodium carbonate, potassium hydroxide, ammonium acetate, pyridine, triethyl amine etc.), another oxime in the presence of an acid (e.g. sulphuric acid, perchloric acid, triflic acid etc.) or a base (e.g. potassium hydroxide, pyridine, triethylamine etc.), or a masked hydroxylamine (e.g. N,O-bis(trimethylsilyl)hydroxylamine) in the presence of a strong base (e.g. potassium hydride, potassium bis(trimethylsilyl)amide etc.) to form the compounds of formula (8). In an alternative embodiment, an intermediate alkylation or aldol condensation synthesis step can be performed on the compounds of formula (6) before the oximation step.

In a preferred embodiment according to the present invention, the compounds of formula (7) and/or of formula (8) can advantageously be prepared from the compounds of formula (5) and/or of formula (6) [preferably from the corresponding ketones compounds, i.e. the ketones having the same radical R], the said preparation process being characterised in that the said compounds of formula (5) and/or of formula (6) are reacted with a hydroxylamine salt (e.g. hydroxylamine hydrochloride) in the presence of an amine (e.g. pyridine, imidazole) and at a temperature lower than 80° C., preferably lower than 70° C. Indeed, we have found out that the synthesis of an oxime involving the reaction of hydroxylamine with a corresponding ketone was not efficient for the synthesis of sterically hindered oximes, e.g. 2,4,4,5-tetramethylhex-5-en-3-one oxime (that is when R=isopropyl).

For the synthesis of particularly sterically hindered compounds of formula (7) and (8), for instance for those in which the R group is a branched or cyclic alkyl it is advantageous to keep the reaction temperature in the range between 60° C. and 80° C. We have found out that when the temperature of the reaction mixture exceeds 80° C., the concurrent decomposition of hydroxylamine leads to a drastic decrease of the yield of the desired oxime and formation of impurities which complicate the purification process.

For instance, when 0.25 g of 2,4,4,5-tetramethylhex-5-en-3-one (that is R=i-Pr) was reacted with two equivalents (0.225 g) of hydroxylamine hydrochloride in the presence of eight equivalents (1 mL) of pyridine used as a base and 1 mL of ethanol it became apparent that it is more advantageous to increase the reaction time while keeping the temperature low (see for illustration purpose the appended FIG. 1 which is a graphic representation of the oxime GC yield vs time).

For instance, when the temperature of the reaction mixture was set to 92° C. the GC yield of the desired 2,4,4,5-tetramethylhex-5-en-3-one oxime peaked at 38% after seven days of reaction after which it started decreasing due to decomposition. This was accompanied with formation of multiple impurities. However, when the oximation reaction was performed at lower temperatures for 14 days, a steady increase in yield was observed giving the desired oxime in 45%, 21% and 5% GC yield at 76° C., 60° C. and 40° C. respectively.

Additionally, we found that the use of nitrogen heterocyclic bases (in particular pyridine) as a base is more efficient in the case of the synthesis of hindered ketones than the use of e.g. sodium acetate or of a combination of sodium hydroxide with hydroxylamine in water. For instance, when 5.0 g of 2,4,4,5-tetramethylhex-5-en-3-one was reacted at 60° C. with two equivalents (4.5 g) of hydroxylamine hydrochloride in the presence of two (5 g) equivalents of sodium acetate used as a base and 20 mL of ethanol for 7 days the 2,4,4,5-tetramethylhex-5-en-3-one oxime was formed in 4% GC yield. When 5.0 g of 2,4,4,5-tetramethylhex-5-en-3-one was reacted at 60° C. with three equivalents (6.42 g) of 50% hydroxylamine in water in the presence of 3.4 (4.4 g) equivalents of sodium hydroxide and 32.4 mL of ethanol for 7 days the 2,4,4,5-tetramethylhex-5-en-3-one oxime was formed in 5% GC yield. In comparison, when 5.0 g of 2,4,4,5-tetramethylhex-5-en-3-one was reacted at 60° C. with two equivalents (4.5 g) of hydroxylamine hydrochloride in the presence of eight (20.5 g) equivalents of pyridine used as a base and 20 mL of ethanol for 7 days the 2,4,4,5-tetramethylhex-5-en-3-one oxime was formed in 9% GC yield.

Accordingly, in a preferred embodiment according to the present invention, the compounds of formula (7) and/or of formula (8) can advantageously be prepared from the compounds of formula (5) and/or of formula (6) [preferably from the corresponding keto compounds, i.e. the ketones having the same radical R], the said preparation process being characterized in that the said compounds of formula (5) and/or of formula (6) are reacted with a hydroxylamine salt (e.g. hydroxylamine hydrochloride) in the presence of an aromatic amine (e.g. pyridine, imidazole) or aniline and at a temperature lower than 80° C., preferably lower than 70° C., wherein said compounds of formulae (5), (6), (7) and (8) are characterized in that R is an alkyl group having from 3 to 9 carbon atoms or an aryl group having from 6 to 9 carbon atoms. In an embodiment according to the present invention, the oximation reaction is conducted for more than one day, more preferably for more than 3 days, for instance for more than 7 days. The molar ratio of the aromatic amine (e.g. pyridine, imidazole) or aniline and hydroxylamine salt (eg. Hydroxylamine hydrochloride, hydroxylamine sulfate) is preferably between 1:1 and 50:1, more preferably between 4:1 and 20:1. The oximation reaction can use various amounts of additional solvent (e.g. methanol, ethanol) but can also be performed without the use of additional solvent. The volume ratio of the aromatic amine (e.g. pyridine, imidazole) or aniline and solvent (e.g. methanol, ethanol) is preferably higher than 1:4, more preferably higher than 1:2, even more preferably higher than 1:1.

In an embodiment according to the present invention, the compounds of formula (5) as defined above can advantageously be synthesized from 2,3-dimethylbutene(s) by using an acylation synthesis step.

2,3-dimethylbutenes

The 2,3-dimethylbutenes compounds according to the present invention can be selected from 2,3-dimethyl-1-butene, 2,3-dimethyl-2-butene, or a mixture thereof; preferably from 2,3-dimethyl-2-butene or from a mixture of 2,3-dimethyl-2-butene and 2,3-dimethyl-1-butene.

Optional Isomerisation Step

In an embodiment according to the present invention, an isomerisation step is preferably performed in order to convert 2,3-dimethyl-1-butene into 2,3-dimethyl-2-butene. This isomerisation step is preferably performed for example when the starting material is 2,3-dimethyl-1-butene or when the starting material is a mixture of 2,3-dimethyl-2-butene and 2,3-dimethyl-1-butene having a content of 2,3-dimethyl-1-butene superior to the content of 2,3-dimethyl-2-butene. Any appropriate olefin isomerisation process can be used; as illustrative and non-restricting examples, base-catalysed and/or acid-catalysed isomerisation process can advantageously be used. In an embodiment according to the present invention, an ion-exchange resin acid catalyst, e.g. an Amberlyst catalyst in the acid form is advantageously used.

Acylation Synthesis Step

Thus, in an embodiment of the present invention, the 2,3-dimethylbutene(s) are subjected to an acylation synthesis step to form the compounds of formula (5) which can be represented by the following formula

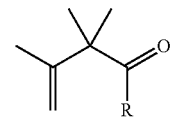

5 wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment of the present invention, the product is obtained by reacting 2,3-dimethylbutene(s) with acyl anhydride or acyl chloride followed by usual workup (e.g. aqueous wash, removal of unreacted reactants and/or solvents and distillation).

An acceptable alternative way of describing the said compound of formula (5) is 1-substituted, 3,3,4-trimethyl-pent-4-en-2-one wherein the substituent in position 1 is selected from methyl, ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, benzyl, phenyl, 4-methoxyphenyl.

Any appropriate acylation process leading to compound of formula (5) can be used; as illustrative and non-restricting examples, the acylation is performed in the presence of 2,3-dimethylbutene(s) and a carboxylic acid anhydride, for example acetic anhydride. This process step can advantageously be operated in the presence of a Lewis or Brønsted acid catalyst, for example zinc chloride, methylsulfonic acid, trifluoromethylsulfonic acid, etc. This process step can advantageously be operated either neat or with the use of a suitable aprotic, polar solvent (e.g. dichloromethane).

In an embodiment according to the present invention, the acylation step is preferably followed by an alkylation step;

e.g. the 2,3-dimethylbutene(s) are subjected to an acylation synthesis step to form the compounds of formula (5a) as represented by the following formula (5a, i.e. wherein R=CH$_3$)

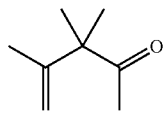

5a which is then converted into compounds of formula (5b) as represented by the following formula

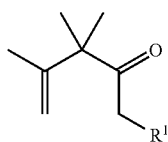

5b wherein R$^1$ is selected from an alkyl group having from 1 to 8 carbon atoms, an alkenyl group containing only one carbon-carbon double bond and having up to 8 carbon atoms, an oxo-alkyl group having up to 8 carbon atoms, or a (substituted) benzyl group having up to 8 carbon atoms.

Compound of the formula (5b) which can be obtained either by subjecting 2,3-dimethylbutene(s) to an acylation synthesis step to form directly the compounds of formula (5b) or by subjecting compounds of formula (5a) to an alkylation step can be further alkylated to form compound of formula (5c).

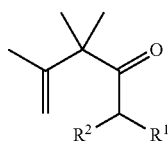

5c wherein R$^1$ is selected from an alkyl group having from 1 to 7 carbon atoms, an alkenyl group containing only one carbon-carbon double bond and having up to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and R$^2$ is selected from an alkyl group having from 1 to 7 carbon atoms, an alkenyl group containing only one carbon-carbon double bond and having up to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals R$^1$ and R$^2$ is not more than 8.

Compound of the formula (5c) which can be obtained either by subjecting 2,3-dimethylbutene(s) to an acylation synthesis step to form directly the compounds of formula (5c) or by subjecting compounds of formula (5b) to an alkylation step or by subjecting compound (5a) to a double alkylation step can be further alkylated to form compound of formula (5d).

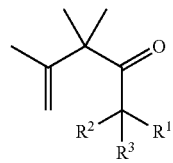

5d wherein R$^1$ an alkyl group having from 1 to 6 carbon atoms, an alkenyl group containing only one carbon-carbon double bond and having up to 6 carbon atoms, an aryl group having up to 6 carbon atoms, an oxo-alkyl group having up to 6 carbon atoms, and R$^2$ is selected from an alkyl group having from 1 to 6 carbon atoms, an alkenyl group containing only one carbon-carbon double bond and having up to 6 carbon atoms, or an oxo-alkyl group having up to 6 carbon atoms, R$^3$ is selected from an alkyl group having from 1 to 6 carbon atoms, an alkenyl group containing only one carbon-carbon double bond and having up to 6 carbon atoms, or an oxo-alkyl group having up to 6 carbon atoms, and the sum of carbon atoms present in radicals R$^1$, R$^2$ and R$^2$ is not more than 8.

When compounds of formula (5c) and (5d) have at least two of the R$^1$, R$^2$ or R$^3$ groups identical, the introduction of these identical groups can be performed in a single alkylation step.

An advantage of the acylation step of the synthesis process of the present invention—when 2,3-dimethyl-2-butene is the starting material—is that it can tolerate the presence of 2,3-dimethyl-1-butene. Consequently, whilst the present invention preferentially uses pure 2,3-dimethyl-2-butene for the acylation step, it can also advantageously tolerate as starting materials molar ratios of 2,3-dimethyl-2-butene to 2,3-dimethyl-1-butene which is lower than 99%, for example lower than 95% said molar ratio is preferably higher than 50%, for example higher than 75%, or even higher than 85%.

In an alternative embodiment according to the present invention, the acylation step is preferably followed by an aldol condensation step; e.g. the 2,3-dimethylbutene(s) are subjected to an acylation synthesis step to form the compounds of formula (5a) as represented by the following formula (5a, i.e. wherein R=CH$_3$)

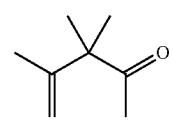

5a which is then converted into compounds of formula (5e) as represented by the following formula

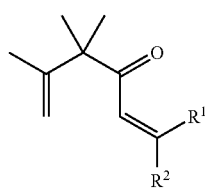

5e wherein $R^1$ is selected from hydrogen, an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and $R^2$ is selected from hydrogen, an alkyl group having from 1 to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals $R^1$ and $R^2$ is not more than 7.

In an embodiment of the present invention, compound of the formula (5b) which can be obtained either by subjecting 2,3-dimethylbutene(s) to an acylation synthesis step to form directly the compounds of formula (5b) or by subjecting compounds of formula (5a) to an alkylation step can be subjected to an aldol condensation step to form compound of formula (5f).

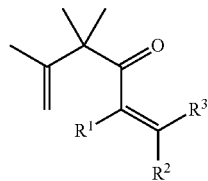

5f wherein $R^1$ is selected from an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and $R^2$ is selected from hydrogen, an alkyl group having from 1 to 6 carbon atoms, an (substituted) aryl group having up to 6 carbon atoms, an oxo-alkyl group having up to 6 carbon atoms, and $R^3$ is selected from hydrogen, an alkyl group having from 1 to 6 carbon atoms, an (substituted) aryl group having up to 6 carbon atoms, an oxo-alkyl group having up to 6 carbon atoms, and the sum of carbon atoms present in radicals $R^1$ and $R^2$ and $R^3$ is not more than 7.

In an embodiment according to the present invention, the acylation step is preferably followed by hydrogenation step and an alkylation step; e.g. the 2,3-dimethylbutene(s) are subjected to an acylation synthesis step followed by hydrogenation synthesis step to form the compounds of formula (6a) as represented by the following formula (6a, i.e. wherein $R=CH_3$)

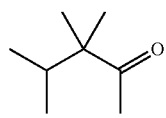

6a which is then converted into compounds of formula (6b) as represented by the following formula

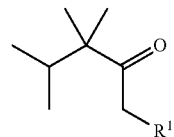

6b wherein $R^1$ is selected from an alkyl group having from 1 to 8 carbon atoms, an alkenyl group containing only one carbon-carbon double bond and having up to 8 carbon atoms, an oxo-alkyl group having up to 8 carbon atoms, or a (substituted) benzyl group having up to 8 carbon atoms.

In an embodiment of the present invention, compound of the formula (5b) which can be obtained either by subjecting 2,3-dimethylbutene(s) to an acylation synthesis step to form directly the compounds of formula (5b) or by subjecting compounds of formula (6a) to an alkylation step can be further alkylated to form compound of formula (6c).

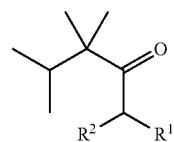

6c wherein $R^1$ is selected from an alkyl group having from 1 to 7 carbon atoms, an alkenyl group containing only one carbon-carbon double bond and having up to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and $R^2$ is selected from an alkyl group having from 1 to 7 carbon atoms, an alkenyl group containing only one carbon-carbon double bond and having up to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals $R^1$ and $R^2$ is not more than 8

In an embodiment of the present invention, compound of the formula 6c which can be obtained either by subjecting 2,3-dimethylbutene(s) to an acylation synthesis step to form directly the compounds of formula (6c) or by subjecting compounds of formula (6b) to an alkylation step or by subjecting compound (6a) to a double alkylation step can be further alkylated to form compound of formula (6d).

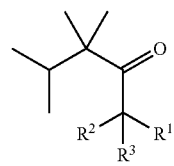

6d wherein $R^1$ an alkyl group having from 1 to 6 carbon atoms, an alkenyl group containing only one carbon-carbon double bond and having up to 6 carbon atoms, an aryl group having up to 6 carbon atoms, an oxo-alkyl group having up to 6 carbon atoms, and $R^2$ is selected from an alkyl group having from 1 to 6 carbon atoms, an alkenyl group containing only one carbon-carbon double bond and having up to 6 carbon atoms, or an oxo-alkyl group having up to 6 carbon atoms, $R^3$ is selected from an alkyl group having from 1 to 6 carbon atoms, an alkenyl group containing only one carbon-carbon double bond and having up to 6 carbon atoms, or an oxo-alkyl group having up to 6 carbon atoms, and the sum of carbon atoms present in radicals $R^1$, $R^2$ and $R^2$ is not more than 8

When compounds of formula (6c) and (6d) have at least two of the $R^1$, $R^2$ or $R^3$ groups identical, the introduction of these identical groups can be performed in a single alkylation step.

In an embodiment according to the present invention, the acylation step followed by a hydrogenation step is preferably followed by an aldol condensation step; e.g. the 2,3-dimethylbutene(s) are subjected to an acylation synthesis step followed by a hydrogenation step to form the compounds of formula (6a) as represented by the following formula (6a, i.e. wherein $R=CH_3$)

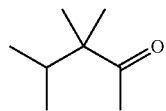

6a which is then converted into compounds of formula (6e) as represented by the following formula

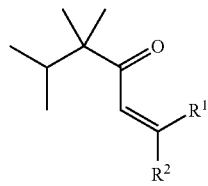

6e wherein $R^1$ is selected from hydrogen, an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and $R^2$ is selected from hydrogen, an alkyl group having from 1 to 7 carbon atoms, an (substituted) aryl group having up to 7 carbon atoms, an oxo-alkyl group having up to 7 carbon atoms, an alkoxyaryl group containing up to 7 carbon atoms or a (substituted) benzyl group having up to 7 carbon atoms and the sum of carbon atoms present in radicals $R^1$ and $R^2$ is not more than 7.

In an embodiment according to the present invention, compound of the formula (6b) which can be obtained either by subjecting 2,3-dimethylbutene(s) to an acylation synthesis step to form directly the compounds of formula (6b) or by subjecting compounds of formula (6a) to an alkylation step can be subjected to an aldol condensation step to form compound of formula (6f).

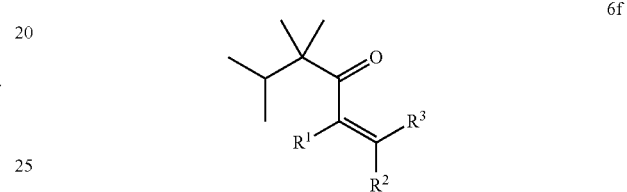

wherein $R^1$ is selected from an alkyl group having from 1 to 7 carbon atoms, an aryl group having up to 7 carbon atoms, an oxo-alkyl group having up to 7 carbon atoms, an alkoxyaryl group containing up to 7 carbon atoms or a (substituted) benzyl group having up to 7 carbon atoms, and $R^2$ is selected from hydrogen, an alkyl group having from 1 to 6 carbon atoms, an (substituted) aryl group having up to 6 carbon atoms, an oxo-alkyl group having up to 6 carbon atoms, and $R^3$ is selected from hydrogen, an alkyl group having from 1 to 6 carbon atoms, an (substituted) aryl group having up to 6 carbon atoms, an oxo-alkyl group having up to 6 carbon atoms, and the sum of carbon atoms present in radicals $R^1$ and $R^2$ and $R^3$ is not more than 7.

The synthesis of ketones (5) and (6) can be thus advantageously realized according to the following schemes:

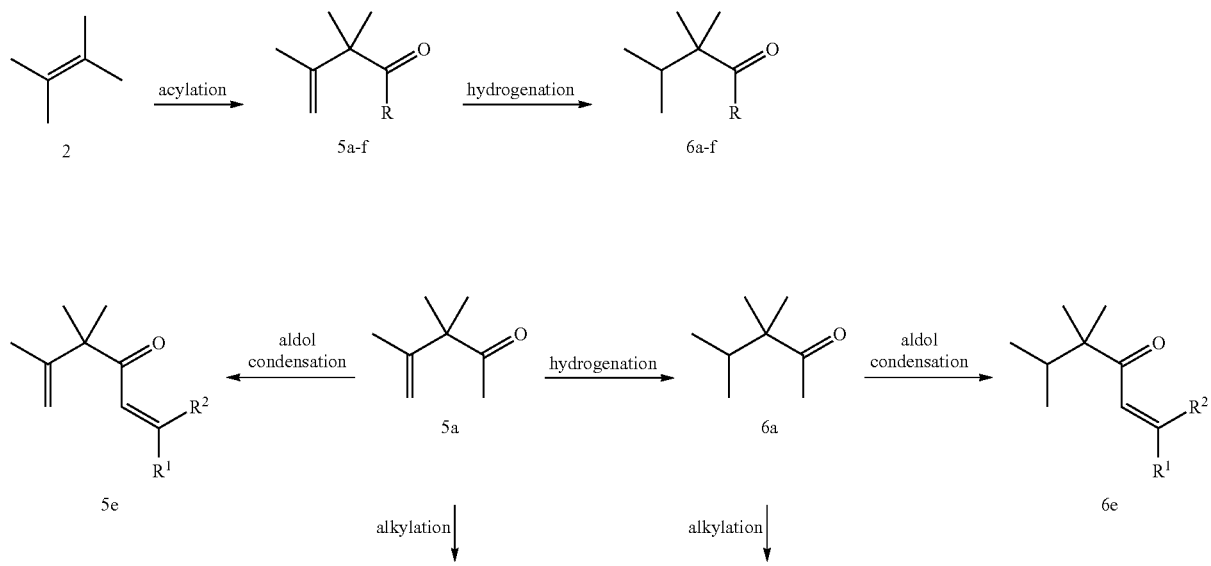

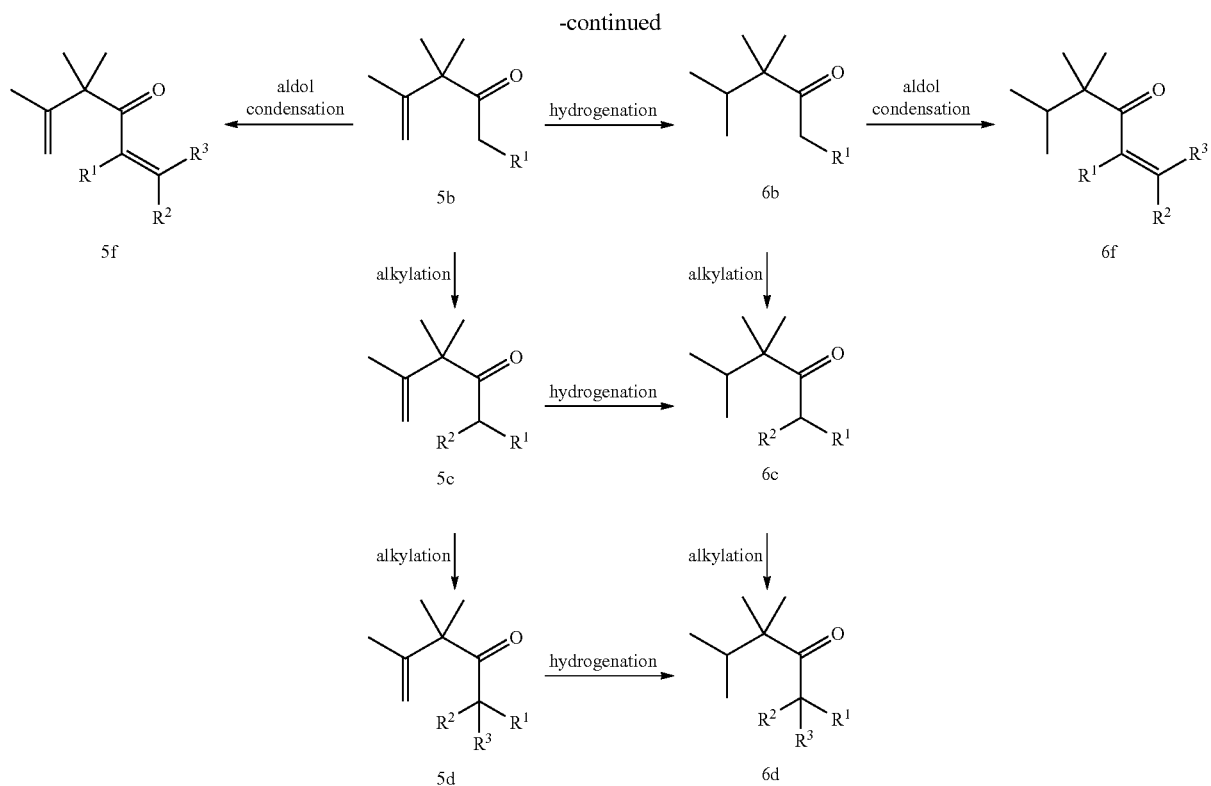

Any appropriate alkylation process leading to compounds of formula 5b-d and 6b-d respectively can be used; as illustrative and non-restricting examples, the alkylation is performed in the presence of the products of acylation of 2,3-dimethylbutenes with the general structure 5 or 6 and an alkyl halide or alkyl sulfate (methyl iodide, dimethyl sulfate, etc) in the presence of a base (potassium hydroxide, potassium tertbutoxide, etc).

Any appropriate aldol condensation process leading to compounds of formula 5e-f and 6e-f respectively can be used; as illustrative and non-restricting examples, the aldol condensation is performed in the presence of the products of acylation of 2,3-dimethylbutenes with the general structure 5 or 6 and an aldehyde or ketone in the presence of a base (potassium hydroxide, potassium tertbutoxide, etc) or in the presence of an acid (hydrochloric acid, sulfuric acid etc.).

Compositions Comprising Ketones

An additional embodiment according to the present invention is that the Applicant has found that some of the intermediate compounds of formula (5) or of formula (6) were also useful as odorants and that they could advantageously be incorporated into perfume, aroma or deodorizing/masking compositions thanks to their effective olfactory property imparted to the compositions or thanks their following advantages/properties: top notes influential, biodegradability, solubility, safety in use and/or stability.

Thus, the present invention also discloses novel fragrance, flavor and/or deodorizing/masking compositions comprising a ketone selected from compounds of formula (5) or of formula (6)

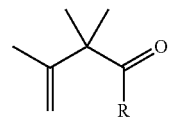

Formula (5)

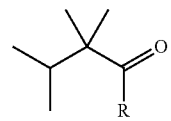

Formula (6)

wherein R is an alkyl group having from 1 to 9 carbon atoms, an alkenyl group containing only one carbon-carbon double bond and having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms.

In an embodiment according to the present invention, R is methyl, ethyl, n-propyl, propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 1-propenyl, 1-isobutenyl, 3-butenyl, 5-(2-methylpent-2-en)yl, 4-penten-2-enyl, 4-pent-1-enyl, 4-(4-methylpent-1-en)yl, 5-(2,5-dimethylhex-2-en)yl, benzyl, phenyl, or 4-methoxyphenyl.

In an embodiment according to the present invention, the fragrance, flavor and/or deodorizing/masking composition comprises the compound of formula (5) or of formula (6) which is selected from

| Structure | Chemical name |
|---|---|
| 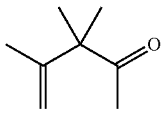 | 3,3,4-trimethyl-4-en-2-one |
| 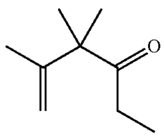 | 4,4,5-trimethylhex-5-en-3-one |
| 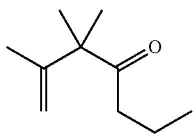 | 2,3,3-trimethylhept-1-en-4-one |
| 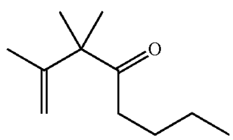 | 2,3,3-trimethyloct-1-en-4-one |
| 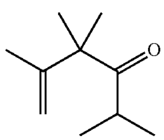 | 2,4,4,5-tetramethylhex-5-en-3-one |
| 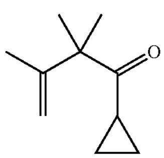 | 1-cyclopropyl-2,2,3-trimethylbut-3-en-1-one |
| 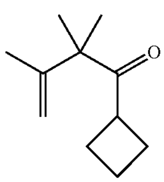 | 1-cyclobutyl-2,2,3-trimethylbut-3-en-1-one |
| 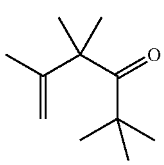 | 2,2,4,4,5-pentamethylhex-5-en-3-one |
| 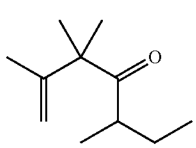 | 2,3,3,5-tetramethylhept-1-en-4-one |
| 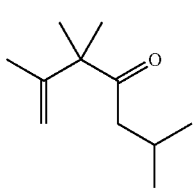 | 2,3,3,6-tetramethylhept-1-en-4-one |

-continued

| Structure | Chemical name |
|---|---|
| 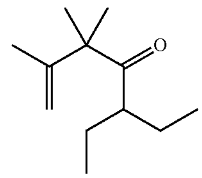 | 5-ethyl-2,3,3-trimethylhept-1-en-4-one |
| 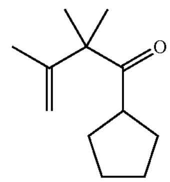 | 1-cyclopentyl-2,2,3-trimethylbut-3-en-1-one |
| 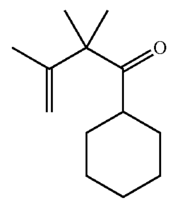 | 1-cyclohexyl-2,2,3-trimethylbut-3-en-1-one |
| 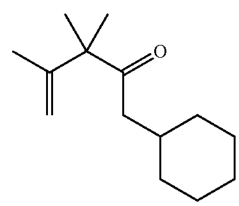 | 1-cyclohexyl-3,3,4-trimethylpent-4-en-2-one |
| 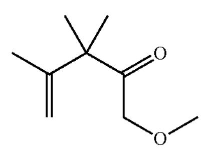 | 1-methoxy-3,3,4-trimethylpent-4-en-2-one |
| 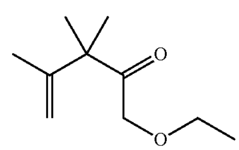 | 1-ethoxy-3,3,4-trimethylpent-4-en-2-one |
| 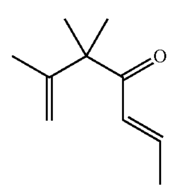 | 2,3,3-trimethylhepta-1,5-dien-4-one |
| 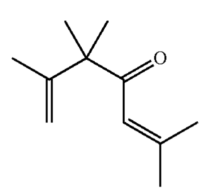 | 2,3,3,6-tetramethylhepta-1,5-dien-4-one |

| Structure | Chemical name |
|---|---|
| | 2,3,3-trimethylocta-1,7-dien-4-one |
| | 2,3,3,8-tetramethylnona-1,7-dien-4-one |
| | 2,3,3,5-tetramethylocta-1,7-dien-4-one |
| | 2,3,3,5,8-pentamethylnona-1,7-dien-4-one |
| | 2,3,3,5,5-pentamethylocta-1,7-dien-4-one |
| | 2,3,3,5,5,8-hexamethylnona-1,7-dien-4-one |
| | 2,2,3-trimethyl-1-phenylbut-3-en-1-one |
| | 3,3,4-trimethyl-1-phenylpent-4-en-2-one |
| 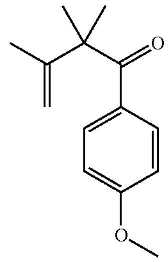 [SMILES: C=C(C)C(C)(C)C(=O)c1ccc(OC)cc1] | 1-(4-methoxyphenyl)-2,2,3-trimethylbut-3-en-1-one |
| 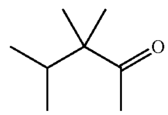 | 3,3,4-trimethylpentan-2-one |
| 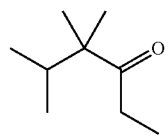 | 4,4,5-trimethylhexan-3-one |
| 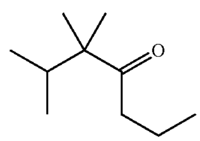 | 2,3,3-trimethylheptan-4-one |
| 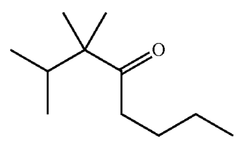 | 2,3,3-trimethyloctan-4-one |
| 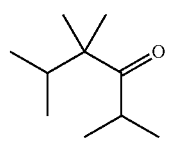 | 2,4,4,5-tetramethylhexan-3-one |
| 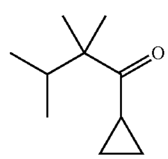 | 1-cyclopropyl-2,2,3-trimethylbutan-1-one |
| 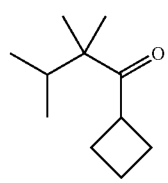 | 1-cyclobutyl-2,2,3-trimethylbutan-1-one |
| 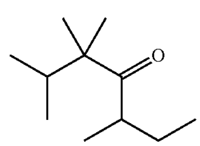 | 2,3,3,5-tetramethylheptan-4-one |

| Structure | Chemical name |
|---|---|
| 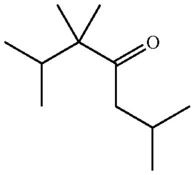 | 2,3,3,6-tetramethylheptan-4-one |
| 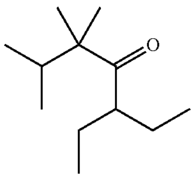 | 5-ethyl-2,3,3-trimethylheptan-4-one |
| 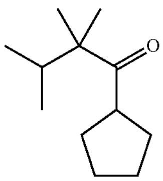 | 1-cyclopentyl-2,2,3-trimethylbutan-1-one |
| 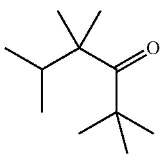 | 2,2,4,4,5-pentamethylhexan-3-one |
| 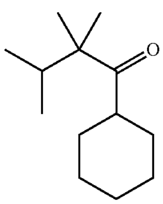 | 1-cyclohexyl-2,2,3-trimethylbutan-1-one |
| 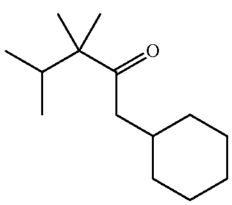 | 1-cyclohexyl-3,3,4-trimethylpentan-2-one |
| 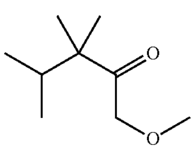 | 1-methoxy-3,3,4-trimethylpentan-2-one |
| 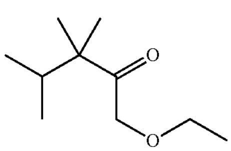 | 1-ethoxy-3,3,4-trimethylpentan-2-one |

| Structure | Chemical name |
|---|---|
| 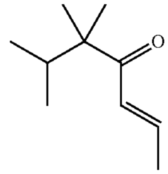 | 5,5,6-trimethylhept-2-en-4-one |
| 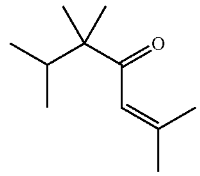 | 2,5,5,6-tetramethylhept-2-en-4-one |
| 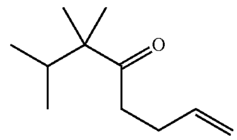 | 2,3,3-trimethyloct-7-en-4-one |
| 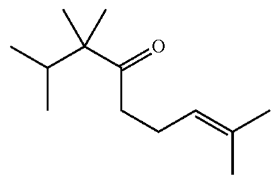 | 2,3,3,8-tetramethylnon-7-en-4-one |
| 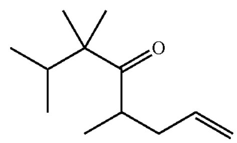 | 2,3,3,5-tetramethyloct-7-en-4-one |
| 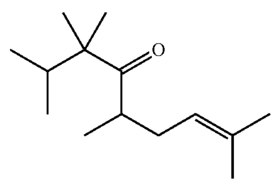 | 2,3,3,5,8-pentamethylnon-7-en-4-one |
| 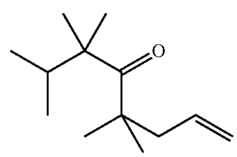 | 2,3,3,5,5-pentamethyloct-7-en-4-one |
| 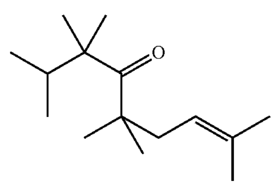 [SMILES: CC(C)=CCC(C)(C)C(=O)C(C)(C)C(C)C] | 2,3,3,5,5,8-hexamethylnon-7-en-4-one |
| 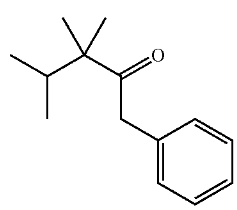 | 3,3,4-trimethyl-1-phenylpentan-2-one |

| Structure | Chemical name |
|---|---|
| 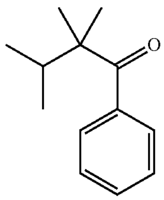 | 2,2,3-trimethyl-1-phenylbutan-1-one |
| | 1-(4-methoxyphenyl)-2,2,3-trimethylbutan-1-one | and/or a mixture of two or more of the said compounds.

The use of more than one ketone compound according to formula (5) or formula (6) as described herein above in a fragrance, flavor and/or deodorizing/masking composition according to the present invention can be particularly advantageous when the difference of the number of carbon atoms of the respective ketone of the same generic formula is between 1 and 9, for example between 1 and 5, preferably between 1 and 4, more advantageously between 1 and 3, in particular between 1 and 2. When a mixture of ketones is used, the weight ratio between the ketone present in highest weight and the ketone present in the second highest weight in the mixture is comprised between 99.9% and 50% for example between 99% and 70%, preferably between 98% and 80%, more advantageously between 98% and 90%, in particular between 98% and 95%.

According to an embodiment of the invention, the fragrance, flavor and/or deodorizing/masking composition according to the present invention contains at least one ketone compound of formula (5) or of formula (6) as described herein above in quantities between 0.00001 and 99.9 wt. %, for example between 0.0001 and 95 wt. %, for example between 0.001 and 25 wt. %, preferably between 0.01 and 15 wt. %, more advantageously between 0.1 and 10 wt. %, in particular between 1 and 5 wt. %, in each case relative to the entire composition.

According to a preferred embodiment of the invention, the fragrance, flavor and/or deodorizing/masking composition according to the present invention contains at least one ketone compound according to formula (5) as previously described and at least one corresponding ketone compound of formula (6) as previously described [i.e. the ketone having the same radical R], in quantities between 0.00001 and 99.9 wt. %, for example between 0.0001 and 95 wt. %, for example between 0.001 and 25 wt. %, preferably between 0.01 and 15 wt. %, more advantageously between 0.1 and 10 wt. %, in particular between 1 and 5 wt. %, in each case relative to the entire composition.

According to a particularly preferred embodiment of the invention, in addition to the compound of formula (5) or of formula (6) as described herein above, the fragrance, flavor and/or deodorizing/masking composition according to the present invention contains additional odorants, for example in a quantity of 0.1 to 99.9 wt. %, preferably 5-90 wt. %, in particular 15-70 wt. %, relative to the entire fragrance and/or flavor composition.

Ketones

In a particular embodiment according to the present invention, the compounds of formula (5) and/or of formula (6) useful in the perfume, aroma and/or deodorizing/masking compositions of the present invention are selected from

| Structure | Chemical name |
|---|---|
| 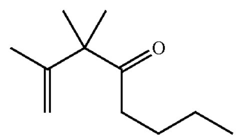 | 2,3,3-trimethyloct-1-en-4-one |
| 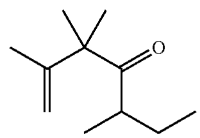 | 2,3,3,5-tetramethylhept-1-en-4-one |
| 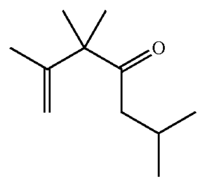 | 2,3,3,6-tetramethylhept-1-en-4-one |
| 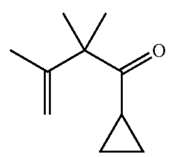 | 1-cyclopropyl-2,2,3-trimethylbut-3-en-1-one |
| 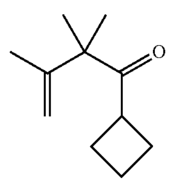 | 1-cyclobutyl-2,2,3-trimethylbut-3-en-1-one |
| 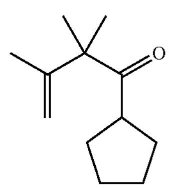 | 1-cyclopentyl-2,2,3-trimethylbut-3-en-1-one |
| 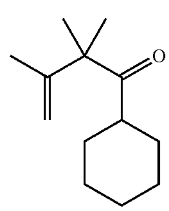 | 1-cyclohexyl-2,2,3-trimethylbut-3-en-1-one |

-continued

| Structure | Chemical name |
|---|---|
| 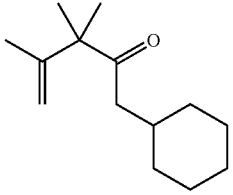 | 1-cyclohexyl-3,3,4-trimethylpent-4-en-2-one |
| 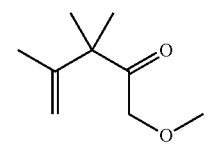 | 1-methoxy-3,3,4-trimethylpent-4-en-2-one |
| 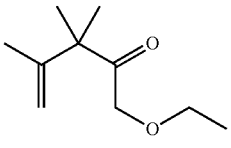 | 1-ethoxy-3,3,4-trimethylpent-4-en-2-one |
| 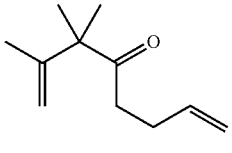 | 2,3,3-trimethylocta-1,7-dien-4-one |
| 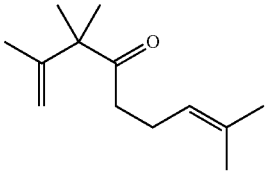 | 2,3,3,8-tetramethylnona-1,7-dien-4-one |
| 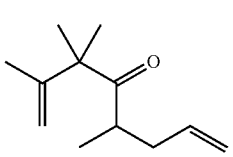 | 2,3,3,5-tetramethylocta-1,7-dien-4-one |
| 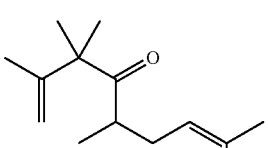 | 2,3,3,5,8-pentamethylnona-1,7-dien-4-one |
| 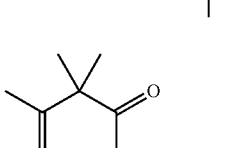 | 2,3,3,5,5-pentamethylocta-1,7-dien-4-one |
| 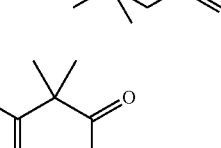 | 2,3,3,5,5,8-hexamethylnona-1,7-dien-4-one |

-continued

| Structure | Chemical name |
|---|---|
| 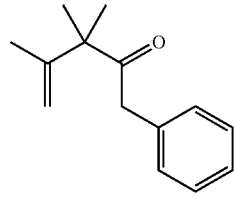 | 3,3,4-trimethyl-1-phenylpent-4-en-2-one |
| 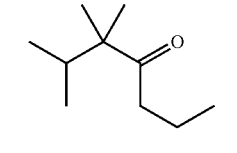 | 2,3,3-trimethylheptan-4-one |
| 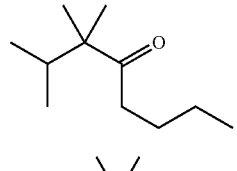 | 2,3,3-trimethyloctan-4-one |
| 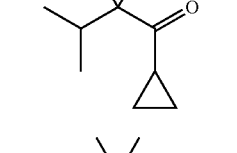 | 1-cyclopropyl-2,2,3-trimethylbutan-1-one |
| 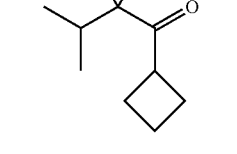 | 1-cyclobutyl-2,2,3-trimethylbuan-1-one |
| 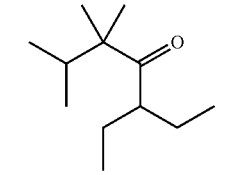 | 5-ethyl-2,3,3-trimethylheptan-4-one |
| 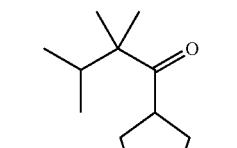 | 1-cyclopentyl-2,2,3-trimethylbutan-1-one |
| 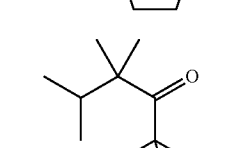 | 2,2,4,4,5-pentamethylhexan-3-one |
| 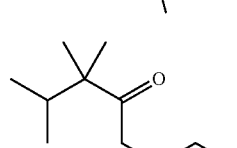 | 1-cyclohexyl-3,3,4-trimethylpentan-2-one |

| Structure | Chemical name |
|---|---|
| 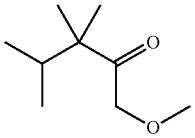 | 1-methoxy-3,3,4-trimethylpentan-2-one |
| 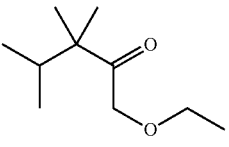 | 1-ethoxy-3,3,4-trimethylpentan-2-one |
| 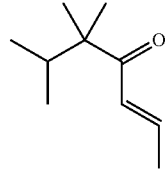 | 5,5,6-trimethylhept-2-en-4-one |
| 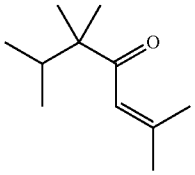 | 2,5,5,6-tetramethylhept-2-en-4-one |
| 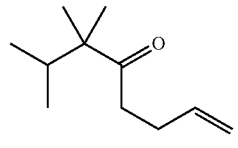 | 2,3,3-trimethyloct-7-en-4-one |
| 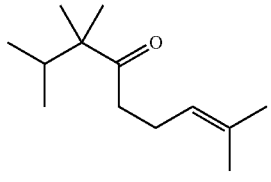 | 2,3,3,8-tetramethylnon-7-en-4-one |
| 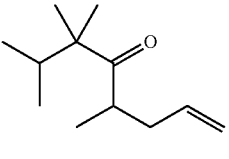 | 2,3,3,5-tetramethyloct-7-en-4-one |
| 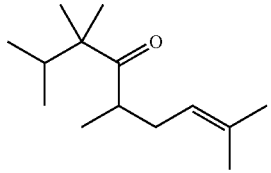 | 2,3,3,5,8-pentamethylnon-7-en-4-one |
| 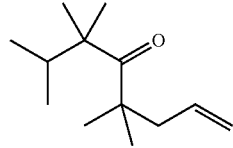 | 2,3,3,5,5-pentamethyloct-7-en-4-one |
| 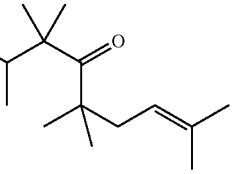 | 2,3,3,5,5,8-hexamethylnon-7-en-4-one |
| 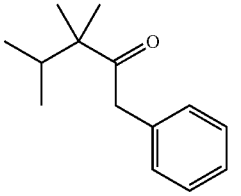 | 3,3,4-trimethyl-1-phenylpentan-2-one |
| 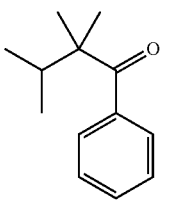 | 2,2,3-trimethyl-1-phenylbutan-1-one |
| 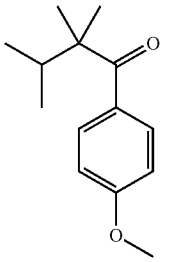 [SMILES: COc1ccc(C(=O)C(C)(C)C(C)C)cc1] | 1-(4-methoxyphenyl)-2,2,3-trimethylbutan-1-one | and/or a mixture of two or more of the said compounds.

In an embodiment according to the present invention, the compounds of formula (7) can advantageously be prepared by the following consecutive steps:

Subjecting 2,3-dimethylbutene(s) to an acylation synthesis step, optionally followed by either an alkylation or an aldol condensation step, to form the compounds of formula (5), and Subjecting the compounds of formula (5) to an oximation synthesis step to form the compounds of formula (7).

In an embodiment according to the present invention, the compounds of formula (8) can advantageously be prepared by the following consecutive steps:

Subjecting 2,3-dimethylbutene(s) to an acylation synthesis step, optionally followed by either an alkylation or an aldol condensation step to form the compounds of formula (5), and subjecting the compounds of formula (5) to a hydrogenation step to form the compounds of formula (6) which are then subjected to an oximation synthesis step to form the compounds of formula (8).

An advantage of the oximation step of the synthesis process of the present invention is that it can tolerate the presence of the reactants of the previous synthesis step, i.e. the reactants coming either from the acylation step and/or from the combined acylation/alkylation or acylation/aldol condensation step as described hereinabove.

Consequently, in an embodiment of the present invention, the oximation step can advantageously be performed when the molar ratio of 2,3-dimethyl-2-butene to compounds of formula (5) and formula (6) is higher than 0, for example higher than 0.05; and/or the molar ratio of carboxylic acid anhydride coming from the acylation step to compounds of formula (5) and formula (6) is higher than 0, for example higher than 0.05; and/or the molar ratio of catalyst residue coming from the acylation step to compounds of formula (5) and formula (6) is higher than 0, for example higher than 0.05.

In an embodiment of the present invention, the oximation step can also advantageously be performed when the molar ratio of 2,3-dimethyl-2-butene to compounds of formula (5) and formula (6) is lower than 0.2, for example lower than 0.15; and/or the molar ratio of carboxylic acid anhydride coming from the acylation step to compounds of formula (5) and formula (6) is lower than 0.2, for example lower than 0.15; and/or the molar ratio of catalyst residue coming from the acylation step to compounds of formula (5) and formula (6) is lower than 0.2, for example lower than 0.15.

An illustrative scheme of the synthesis of the compounds of formula (7) and/or of formula (8) according to the present invention is represented below

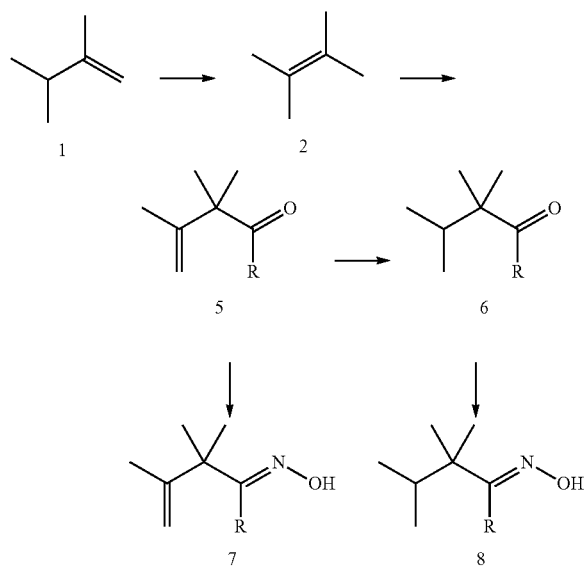

wherein R is methyl, ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 3-butenyl, 5-(2-methylpent-2-en)yl, 4-pent-2-enyl, 4-pent-1-enyl, 5-(2,5-dimethylhex-2-en)yl, benzyl, phenyl, or 4-methoxyphenyl.

In an embodiment of the present invention, the claimed fragrance, flavor and/or deodorizing/masking composition is advantageously used as a perfumery composition. Perfumery compositions according to the present invention generally include a perfume, a cologne, an eau du toilette, and/or an eau de parfum. In an embodiment of the present invention, the claimed fragrance, flavor and/or deodorizing/masking composition is advantageously used in a cosmetic formulation, a personal care product, a cleansing product, a fabric softener, and/or air freshener, and the like. Furthermore, it is within the purview of embodiments of the invention that the novel fragrance, flavor and/or deodorizing/masking composition(s) and/or novel compound(s) of formula (7) or of formula (8) or of formula (5) or of formula (6) described herein may be integrated into building materials, wall and floor coverings, vehicle components, and the like.

In general, in addition to the novel odorant and/or fragrance, flavor and/or deodorizing/masking compositions described herein, suitable fragrance, flavor or deodorizing compositions may advantageously include conventional ingredients such as, for example, solvents, carriers, stabilizers, emulsifiers, moisturizers, dispersants, diluents, thickeners, thinners, other odorants, and/or adjuvants, and the like.

The compounds of formula (5), (6), (7), or (8) combine with numerous known natural or synthetic fragrance, flavor and/or deodorizing/masking materials, whereby the range of the natural ingredients can embrace not only readily-volatile but also semi-volatile and slightly-volatile components and the range of the synthetic ingredients can embrace representatives from many classes of substances, as will be evident from the following nonlimiting compilation:

Natural products such as: Ajowan oil, Amyris oil, Armoise oil, Artemisia oil, Basil oil, Bees wax absolute, Bergamot oil, Birch tar oil, Black pepper oil, Black pepper oleoresin, Camphor oil, Cananga oil, Caraway oil, Cardamom oil, Carrot seed oil, Castoreum absolute, Cedar leaf oil, Cedarwood oil, Celery seed oil, Chamomile oil, Cinnamon bark oil, Cinnamon leaf oil, Cistus absolute, Cistus oil, Citronella oil, Citronella terpenes, Clary sage oil, Clove oil rectified, Cognac oil white, Coriander seed oil, Cumin seed oil, Cypress oil, Davana oil, Dill seed oil, Elemi oil, Elemi resinoid, Eucalyptus oil, Fir needle oil, Galbanum oil, Geranium oil, Ginger oil Indian, Grapefruit oil, Guaiacwood oil, Gurjun balsam, Jasmin absolute, Jatamansi oil, Juniper berry oil, Juniper leaf oil, Kachur oil, Labdanum absolute, Labdanum resinoid, Lavender oil, Lemon oil, Lemon oil terpenes, Lemongrass oil, Lime oil, Litsea cubeba oil, Litsea cubeba terpenes, Lobhan choya resinoid, Mandarin oil, Mentha arvensis oil, Mentha citrata oil, Mimosa absolute, Myrrh resinoid, Nagarmotha oil, Nutmeg oil, Oakmoss absolute, Oakmoss resinoid, Olibanum oil, Olibanum resinoid, Orange oil, Origanum oil, Palma rosa oil, Patchouli oil, Peppermint oil, Peru Balsam resinoid, Petitgrain oil, Pine needle oil, Pink pepper oil, Rose absolut, Rose oil, Rosemary oil, Sandalwood oil, Seaweed absolute, Spearmint oil, Sugandh kokila oil, Sugandh mantri oil, Tagete oil, Tolu Balsam resinoid, Tuberose absolute, Turmeric oil, Turpentine oil, Valerian oil, Vetiver oil, Vetiver terpenes.

Synthetic raw materials for instance: Esters such as: Aldehyde C16, Allyl amyl glycolate, Allyl caproate, Allyl cyclohexyl propionate, Allyl heptoate, Allyl phenoxy acetate, Amyl acetate iso, Amyl benzoate, Amyl butyrate, Amyl caproate, Amyl cinnamate, Amyl isovalerate, Amyl phenyl acetate, Amyl propionate, Amyl salicylate iso, Amyris acetate, Anisyl acetate, Benzyl acetate, Benzyl benzoate, Benzyl butyrate, Benzyl cinnamate, Benzyl formate, Benzyl isobutyrate, Benzyl isoeugenol, Benzyl propionate, Benzyl salicylate, Benzyl tiglate, Butyl acetate, Butyl butyrate, Butyl butyryl lactate, Caryophyllene acetate, Cedryl acetate, Cinnamyl acetate, Cinnamyl butyrate, Cis-3-hexenyl acetate, Cis-3-hexenyl benzoate, Cis-3-hexenyl caproate, Cis-3-hexenyl formate, Cis-3-hexenyl isobutyrate, Cis-3-hexenyl-2-methyl butyrate, Cis-3-hexenyl propionate, Cis-3-hexenyl salicylate, Cis-3-hexenyl tiglate, Citronellyl acetate, Citronellyl butyrate, Citronellyl formate, Citronellyl isobutyrate, Citronellyl propionate, Citronellyl tiglate, Cyclabute, Cyclogalbanate, Cyclohexyl ethyl acetate, Decyl acetate, Dibutyl phthalate, Diethyl malonate, Diethyl phthalate, Dihydromyrcenyl acetate, Dimethyl octanyl acetate, Dimethyl phenyl ethyl carbinyl acetate, Dioctyl adipate, Dioctyl phthalate, Dimethyl benzyl carbinyl acetate, Dimethyl benzyl carbinyl butyrate, Ethyl linalyl acetate, Ethyl 2-methyl butyrate, Ethyl 3-phenyl propionate, Ethyl acetate, Ethyl acetoacetate, Ethyl benzoate, Ethyl butyrate, Ethyl caprate C10, Ethyl caproate C6, Ethyl caprylate C8, Ethyl cinnamate, Ethyl heptoate, Ethyl hexyl acetate, Ethyl isobutyrate, Ethyl laurate, Ethyl pelargonate, Ethyl phenoxy acetate, Ethyl phenyl acetate, Ethyl phenyl glycidate, Ethyl propionate, Ethyl safranate, Ethyl salicylate, Ethyl valerate, Eugenyl acetate, Evernyl, Fenchyl acetate, Floramat, Frescolat ML, Fructone, Fruitate, Geranyl acetate, Geranyl butyrate, Geranyl formate, Geranyl propionate, Geranyl tiglate, Givescone, Guaiol acetate, Hedionate, Hedione, Helvetolide, Herbanate, Hexyl acetate, Hexyl benzoate, n-Hexyl butyrate, Hexyl caproate, Hexyl isobutyrate, Hexyl propionate, Hexyl salicylate, Isobornyl acetate, Isobutyl acetate, Isobutyl phenyl acetate, Isobutyl salicylate, Isoeugenyl acetate, Isononyl acetate, Isopentyrate, Isopropyl 2-methyl butyrate, Isopropyl myristate, Jasmonyl, Liffarome, Linalyl acetate, Mahagonate, Manzanate, Menthanyl acetate, Menthyl acetate, Methyl benzoate, 2-Methyl butyl acetate, Methyl chamomile, Methyl cinnamate, Methyl cyclogeranate, Methyl heptine carbonate, Methyl laurate, Methyl octine carbonate, Methyl phenyl acetate, Methyl salicylate, Methyl-2-methyl butyrate, Neofolione, Nopyl acetate, Octenyl acetate, Octyl acetate, Octyl isobutyrate, Para cresyl acetate, Para cresyl isobutyrate, Para cresyl phenyl acetate, Pear ester, Peranat, Phenoxy ethyl isobutyrate, Phenyl ethyl acetate, Phenyl ethyl butyrate, Phenyl ethyl formate, Phenyl ethyl isobutyrate, Phenyl ethyl phenyl acetate, Phenyl ethyl propionate, Phenyl ethyl salicylate, Phenyl ethyl tiglate, Phenyl propyl isobutyrate, Prenyl acetate, Romandolide, Sagecete, Styrallyl acetate, Styrallyl propionate, Tangerinol, Terpinyl acetate, Thesaron, Trans-2-hexenyl acetate, Tropicate, Verdox, Verdyl acetate, Verdyl propionate, Vertenex, Vetikol acetate, Vetiveryl acetate, Yasmolys.

Lactones such as: Ambrettolide, Arova N, Celeriax, Decalactone delta, Decalactone gamma, Dodecalactone delta, Dodecalactone gamma, Ethylene brassylate, Exaltolide, Heptalactone gamma, Hexalactone delta, Hexalactone gamma, Methyl laitone, Methyl octalactone, Nonalactone delta, Nonalactone gamma, Octahydrocoumarine, Octalactone delta, Octalactone gamma, Rootylone, Silvanone supra, Undecalactone delta, Undecalactone gamma, Valerolactone gamma, 10-Oxa HexaDecanolide (OHD musk), Coumarin, Habanolide, Jasmolactone.

Aldehydes such as: Acetaldehyde, Adoxal, Aldehyde C10, Aldehyde C11 iso, Aldehyde C11 moa, Aldehyde C11 undecylenic, Aldehyde C11 undecylic, Aldehyde C12 Laurie, Aldehyde C12 MNA, Anisaldehyde, Amyl cinnamaldehyde, Benzaldehyde, Bourgeonal, Campholenaldehyde, Cantonal, Cetonal, Cinnamic aldehyde, Cis-4-decenal, Cis-6-nonenal, Citral, Citronellal, Citronellyl oxyacetaldehyde, Cocal, Cuminaldehyde, Curgix, Cyclal C, Cyclamen aldehyde, Cyclomyral, Cyclovertal, Decenal 9, Dupical, Empetal, Ethyl vanillin, Floralozone, Florhydral, Geraldehyde, Helional, Heliotropin, Heptanal, Hexanal, Hexyl cinnamaldehyde, Hivemal neo, Hydratropaldehyde, Hydroxycitronellal, Intreleven aldehyde, Isobutavan, Isocyclocitral, Isovaleraldehyde, Lilial, Limonenal, Maceal, Mefranal, Melonal, Methyl cinnamaldehyde, Nonadien-al trans-2 cis-6, Nonanal, Octanal, Oncidal, Para tolyl aldehyde, Phenyl acetaldehyde, Phenyl propyl aldehyde, Precyclemone B, Safranal, Salicylaldehyde, Scentenal, Syringa aldehyde, Trans-4-decenal, Trans-2-dodecenal, Trans-2-hexenal, Trans-2-nonenal, Trifernal, Vanillin, Veratraldehyde, Vernaldehyde Ketones such as: Acetanisol, Acetoin, Acetophenone, Aldron, Allyl ionone, Benzophenone, Benzyl acetone, Calone, Camphor, Carvone d-, Carvone l-, Cashmeran, Cedryl methyl ketone, Cepionate, Claritone, Cosmone, Crysolide, Cyclotene, Damascenone, Damascone alpha, Damascone beta, Damascone delta, Damascone gamma, Diacetyl, Dihydro beta ionone, Dihydro isojasmonate, Dimethyl octenone, Dynascone, Ethyl amyl ketone, Ethyl maltol, Fenchone, Filbertone, Geranyl acetone, Globanone, Heptyl cyclopentanone, Ionone alpha, Ionone beta, Ionone pure, Iriswood, Irone alpha, Iso E Super, Isofenchone, Isojasmone T, Isolone K, Isomenthone, Isophorone, Jasmone cis-, Kambernoir, Kephalis, Koavone, Lavendinal, Maltol, Menthone, Methyl acetophenone, Methyl amyl ketone, Methyl heptenone, Methyl hexyl ketone, Methyl ionone gamma, Methyl naphthyl ketone beta, Methyl nonyl ketone, Muscenone, Muscone, Nectaryl, Orinox, OTBC Ketone, Para tertbutylcyclohexanone, Patchwood, Phantolid, Pharaone, Piperitone, Plicatone, Raspberry ketone, Raspberry ketone methyl ether, Safraleine, Spirogalbanone pure, Tonalid, Trimofix O, Veloutone, Vetikon.

Alcohols such as: Alcohol oxo C13, Amber core, Ambermax, Ambrinol, Amyl vinyl carbinol, Anisic alcohol, Bacdanol, Benzyl alcohol, Butanol, Cedrol crystals, Cinnamic alcohol, Citronellol, Coranol, Decanol, Dimethyl benzyl carbinol, Dimethyl octanol, Dimethyl phenyl ethyl carbinol, Dimetol, Fenchol, Hexanol, Isoborneol, Isobornyl cyclohexanol, Javanol, Keflorol, Kohinool, Lauryl alcohol, Lilyflore, Linalool oxide, Mayol, Menthol, Norlimbanol, Octanol, Osyrol, Para tertbutylcyclohexanol, Phenoxanol, Phenoxyethanol, Phenyl ethyl alcohol, Phenyl propyl alcohol, Propylene glycol, Rosaphen, Rose glycol, Styrallyl alcohol, Tricyclodecane dimethanol, Tetrahydro linalool, Tetrahydro myrcenol, Timberol, Undecavertol, Cis-3-hexenol, Citronellol laevo, Cyclofloranol, Dihydrolinalool, Dihydromyrcenol, Dimyrcetol, Ebanol, Geraniol, Isopulegol, Linalool, Nerol, Nerolidol, Nonadien-ol trans-2 cis-6, Polysantol, Rosalva, Sandalmysore core, Sandalore, Terpinen-4-ol, Terpineol, Trans-2-hexenol Phenols such as: Butylated hydroxyanisole, Dihydroeugenol, Dimethyl hydroquinone, Dimethyl resorcinol, Eugenol pure, Guaiacol, Isoeugenol, Meta cresol, Methyl diantilis, Para cresol, Propenyl guaethol, Thymol, Ultravanil.

Ethers such as: Ambroxan, Anethole, Anther, Benzyl isoamyl ether, Benzyl isopropyl ether, Benzyl isovalerate, Boisiris, Cedramber, Cetalox, Decyl methyl ether, Dibenzyl ether, Dihydro rose oxide, Diphenyl oxide, Doremox, Estragole, Ethyl linalool, Eucalyptol, Galaxolide, Gyrane, Herbavert, Lime oxide, Madrox, Methyl isoeugenol, Naphthyl isobutyl ether beta, Nerol oxide, Nerolin bromelia, Para cresyl butyl ether, Para cresyl methyl ether, Petiole, Phenyl ethyl methyl ether, Rhubafuran, Rose oxide, Rosyrane, Trisamber, Vetylbois K, Yara yara Acetals such as: Acetal CD, Acetal R, Amberketal, Boisambrene forte, Citrathal, 1,1-Diethoxyethane, Emeraldine, Freshopal, Herboxane, Indoflor, Jacinthaflor, Magnolan, Spirambrene, Viridine, Elintaal, Glycolierral, Karanal, Methyl pamplemousse, Hydrocarbons such as: Bisabolene, Camphene, Carene delta 3, Caryophyllene, Cedrene, Cymene para, Dipentene, Diphenyl methane, Isolongifolene, Limonene d-, Longifolene, Myrcene, Naphthalene, Ocimene, Pinene alpha, Pinene beta, Styrene, Terpinene gamma, Terpinolene, 1,3,5-Undecatriene, Verdoracine.

Sulphur compounds such as: Corps cassis, Dibutyl sulphide, Dimethyl sulphide, Exovert, Grapefruit thiol, Oxane, Ribes mercaptan, Sulfurol, Thiocineol.

Nitriles such as: Cinnamyl nitrile, Citronellyl nitrile, Citronitrile, Clonal, Cumin nitrile, Hexyl cyclopentanone, Irisnitrile, Lemonile, Peonile, Tridecyl nitrile, Agrumen nitrile, n-decyl nitrile.

Oximes such as: Buccoxime, Labienoxime, Stemone.

Nitrogen heterocycles such as: 2-acetylpyrazine, 2-acetylpyridine, sec-butylquinoline, Corps racine, 2-ethyl-3,5(or 6)-dimethylpyrazine, Furfuryl pyrrole, Indole, Isobutyl quinoline, 2-Isobutyl-3(or 6)-methoxypyrazine, Isopropyl quinoline, Maritima, p-methyl quinoline, Skatol, 2,3,5-trimethylpyrazine.

Nitro compound such as: Musk Ketone

Schiff bases such as: Aurantiol, Helianthral, Ligantraal, Verdantiol.

Other materials such as: Acetanilide, Gardamide, Paradisamide, Dimethyl anthranilate, Methyl anthranilate, n-Butyric acid, Capric acid, Caproic acid, Caprylic acid, Phenylacetic acid, Caryophyllene oxide, Cedroxyde, Tobacarol The compounds of formula (5), (6), (7), or (8) can accordingly be used for the production of compositions and, as will be evident from the foregoing compilation, a wide range of known odorants/fragrance, flavor and/or deodorizing/masking materials. In the production of such compositions, the known fragrance, flavor and/or deodorizing/masking materials referred to earlier can be used according to methods which are known to the perfumer such as, for example, according to W. A. Poucher, Perfumes, Cosmetics and Soaps 2, 7th Edition, Chapman and Hall, London 1974.

The present invention also relates to a mixture useful in fragrance, flavor and/or deodorizing/masking compositions wherein said mixture comprises at least one oxime compound of formula (7) and/or (8) together with at least one ketone compound of formula (5) and/or (6), wherein R is an alkyl group having from 1 to 9 carbon atoms, an alkenyl group containing only one carbon-carbon double bond (that is preferably not conjugated with the oxime C=N bond) having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms. In an embodiment of the present invention, the radical R of the oxime compound is identical to the radical R of the ketone compound. In an embodiment of the present invention, the weight ratio between the oxime(s) and the ketone(s) in the mixture is comprised between 0.01% and 99.99%, for example between 0.1% and 99.9%, for example between 1% and 99%, for example between 1% and 20%, for example between 80% and 99%.

The present invention also relates to fragrance, flavor and/or deodorizing/masking compositions comprising at least one oxime compound of formula (7) and/or (8) together with at least one ketone compound of formula (5) and/or (6), wherein R is an alkyl group having from 1 to 9 carbon atoms, an alkenyl group containing only one carbon-carbon double bond (that is preferably not conjugated with the oxime C=N bond) having up to 9 carbon atoms, an (substituted) aryl group having up to 9 carbon atoms, an oxo-alkyl group having up to 9 carbon atoms, an alkoxyaryl group containing up to 9 carbon atoms or a (substituted) benzyl group having up to 9 carbon atoms. In an embodiment of the present invention, the radical R of the oxime compound is identical to the radical R of the ketone compound. In an embodiment of the present invention, the weight ratio between the oxime(s) and the ketone(s) is comprised between 0.01% and 99.99%, for example between 0.1% and 99.9%, for example between 1% and 99%, for example between 1% and 20%, for example between 80% and 99%.

In an embodiment of the present invention, the claimed fragrance, flavor and/or deodorizing/masking composition comprises in addition to the oximes/ketones at least one ester and/or one alcohol, preferably at least a mixture of ester and alcohol; the said ester and/or alcohol are preferably selected from the list defined herein above. In an embodiment of the present invention, the claimed odorant composition is characterised by a total content of the compound(s) of formula (7) or of formula (8) or of formula (5) or of formula (6) together with the ester(s) and/or alcohol(s) which is superior to 25 wt %, preferably superior to 50 wt %, for example superior to 75 wt %, or even superior to 90 wt %.

The disclosure is further illustrated by the following examples which in no way should be construed as being further limiting. One skilled in the art will readily appreciate that the specific methods and results described are merely illustrative.

All stereoisomers of the compounds of the instant disclosure are contemplated, either in admixture or in pure or substantially pure form. The compounds of the present disclosure can have asymmetric centers at any of the carbon atoms, consequently, claimed compounds can exist in enantiomeric, or diastereomeric forms, or in mixtures thereof. The processes for preparation can utilize racemates, (pure) enantiomers, nonracemic mixtures of enantiomers, diastereomers or mixtures of diasteremers as starting materials. When diastereomeric or enantiomeric products are obtained as mixtures, they can be separated by conventional methods for example, chromatographic separation or fractional crystallization or through diastereomeric salt formation. When intended, a desired enantiomer or diastereomer can also be obtained by following appropriate enantioselective or diastereoselective reactions.

SYNTHESIS EXAMPLES

Example 1

Synthesis of 3,3,4-trimethylpent-4-en-2-one

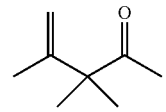

2,3-Dimethyl-2-butene (510 g, 5.94 mol, 1 equiv) was added to a solution of zinc chloride (243 g, 1.78 mol, 0.3 equiv) in acetic anhydride (1.04 kg, 10.2 mol, 1.71 equiv) at 5° C. under nitrogen atmosphere while stirring. The mixture was stirred in an ice bath and left to reach 20° C. within 24 h. Subsequently, water (1.50 L) was added and the mixture was extracted with methyl tert-butyl ether (3×500 mL). The combined organic phases were washed successively with water (2×750 mL), aqueous saturated Na$_2$CO$_3$ (to pH 7) and brine (750 mL). The organic phase was dried over Na$_2$SO$_4$ and volatiles were removed under reduced pressure. The residue (960 g) was distilled in vacuo (57° C./55 mbar) to afford 3,3,4-trimethylpent-4-en-2-one (501 g, 66%).

$^1$H NMR (400 MHz, CDCl$_3$): δ 1.15 (s, 6H), 1.58 (s, 3H), 1.98 (s, 3H), 4.89 (s, 2H).

$^{13}$C NMR (100 MHz, CDCl$_3$): δ 19.2, 22.2, 23.9, 53.0, 110.6, 146.8, 210.9.

Example 2

Synthesis of (E)-3,3,4-trimethylpent-4-en-2-one Oxime

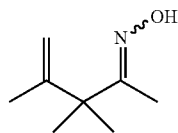

Hydroxylamine hydrochloride (6.62 g. 95.3 mmol, 1.2 equiv) was added to a suspension of sodium acetate (7.81 g, 95.2 mmol, 1.2 equiv) in methylcyclohexane (31.0 g) and followed by dropwise addition of 3,3,4-trimethylpent-4-en-2-one (10.0 g, 79.2 mmol, 1 equiv) at 25° C. The reaction mixture was then heated to reflux for 20 h. Then water (20 mL) and methyl tert-butyl ether (60 mL) were added at 25° C. and the mixture was stirred for 15 min. Subsequently, organic phase was separated, dried over anhydrous Na$_2$SO$_4$ and the solvent was removed under reduced pressure to afford pure (E)-3,3,4-trimethylpent-4-en-2-one oxime (6.20 g, 55%).

$^1$H NMR (400 MHz, CDCl$_3$): δ 1.86 (s, 6H), 1.57 (s, 3H), 1.70 (s, 3H), 4.81-4.83 (m, 2H), 9.82 (s, br. 1H). $^{13}$C NMR (100 MHz, CDCl$_3$): δ 10.8, 19.8, 24.6, 46.4, 111.1, 149.5, 162.6.

Example 3

Synthesis of 4,4,5-trimethylhex-5-en-3-one

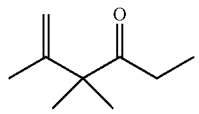

2,3-Dimethyl-2-butene (1.17 kg, 14.0 mol, 1 equiv) was added to a solution of zinc chloride (565 g, 4.15 mol, 0.3 equiv) in propionic anhydride (2.50 kg, 19.2 mol, 1.38 equiv) at 5° C. under nitrogen atmosphere while stirring. The mixture was stirred in an ice bath and left to reach 20° C. within 24 h. The mixture was washed with water (3×3.00 L), mixture of ice-cold water (1 L) and aqueous saturated sodium carbonate (1.75 L), water (1×500 mL), and brine (1×500 mL). Organic fraction was separated and was distilled in vacuo (69° C./35 mbar) to afford 4,4,5-trimethylhex-5-en-3-one (1.01 kg, 51%).

$^1$H NMR (400 MHz, CDCl$_3$): δ 0.92 (t, J=7.2 Hz, 3H), 1.15 (s, 6H), 1.56 (s, 3H), 2.35 (q, J=7.2 Hz, 2H), 4.87 (s, 2H). $^{13}$C NMR (100 MHz, CDCl$_3$): δ 8.3, 20.1, 23.3, 29.5, 53.5, 111.4, 148.0, 214.4.

Example 4

Synthesis of (E)-4,4,5-trimethylhex-5-en-3-one Oxime

Prepared as in example 2; yield 4.70 g (43%).

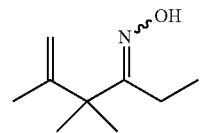

$^1$H NMR (400 MHz, CDCl$_3$): δ 1.04 (t, J=7.2 Hz, 3H), 1.19 (s, 6H), 1.58 (s, 3H), 2.11-2.16 (m, 2H), 4.82-4.83 (m, 2H), 9.35 (s, hr. 1H). $^{13}$C NMR (100 MHz, CDCl$_3$): δ 11.1, 19.7, 20.0, 24.7, 46.6, 111.2, 149.5, 166.2.

Example 5

Synthesis of 2,3,3-trimethylhept-1-en-4-one

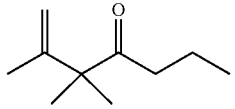

2,3-Dimethyl-2-butene (930 g, 11.0 mol, 1 equiv) was added to a solution of zinc chloride (452 g, 3.31 mol, 0.3 equiv) in butyric anhydride (1.75 kg, 11.0 mol, 1 equiv) at 5° C. under nitrogen atmosphere while stirring. The mixture was warmed to 20° C. within 6 h and then stirred at 20° C. for 48 h. The reaction mixture was washed successively with water (2×4.0 L), aqueous saturated Na$_2$CO$_3$ (to pH 7) and brine (1.0 L). The organic fraction was separated (1.55 kg) and was distilled in vacuo (59° C./10 mbar) to afford 2,3,3-trimethylhept-1-en-4-one (1.24 kg, 60%).

$^1$H NMR (400 MHz, CDCl$_3$): δ 0.80 (t, J=7.6 Hz, 3H), 1.15 (s, 6H), 1.43-1.52 (m, 2H), 1.55 (s, 3H), 2.31 (t, J=7.2 Hz, 2H), 4.88 (s, 2H).

Example 6

Synthesis of 2,3,3-trimethylhept-1-en-4-one Ooxime

Prepared as in example 2; yield 18.0 g (82%).

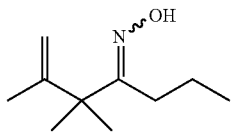

$^1$H NMR (400 MHz, CDCl$_3$): δ 0.86 (t, J=7.6 Hz, 3H), 1.18 (s, 6H), 1.45-1.54 (m, 2H), 1.58 (s, 3H), 2.03-2.07 (m, 2H), 4.82 (s, 2H), 9.63 (s, br. 1H). $^{13}$C NMR (100 MHz, CDCl$_3$): δ 15.1, 19.9, 20.0, 24.8, 28.9, 46.5, 111.1, 149.6, 165.3.

Example 7

Synthesis of 2,3,3-trimethyloct-1-en-4-one

Prepared as in example 1; yield 91.0 g (37%).

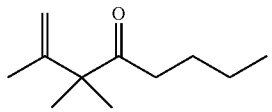

¹H NMR (400 MHz, CDCl₃): δ 0.81 (t, J=7.2 Hz, 3H), 1.15-1.24 (m, 8H), 1.39-1.46 (m, 2H), 1.57 (s, 3H), 2.32 (t, J=7.6 Hz, 2H), 4.88 (s, 2H).
¹³C NMR (100 MHz, CDCl₃): δ 14.0, 20.3, 22.5, 23.4, 26.4, 36.2, 53.8, 111.7, 148.1, 214.0.

Example 8

Synthesis of 2,3,3-trimethyloct-1-en-4-one Oxime

Prepared as in example 2; yield 6.00 g (60%).

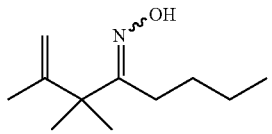

¹H NMR (400 MHz, CDCl₃): δ 0.83 (t, J=7.2 Hz, 3H), 1.18 (s, 6H), 1.22-1.31 (m, 2H), 1.41-1.49 (m, 2H), 1.58 (s, 3H), 2.05-2.09 (m, 2H), 4.82 (s, 2H), 9.43 (s, br. 1H).
¹³C NMR (100 MHz, CDCl₃): δ 11.8, 18.2, 21.5, 22.8, 24.6, 26.4, 44.8, 109.1, 147.8, 162.8.

Example 9

Synthesis of 2,3,3,6-tetramethylhept-1-en-4-one

Prepared as in example 1; yield 34%.

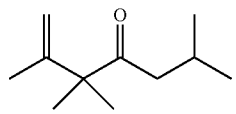

Example 10

Synthesis of 2,3,3,6-tetramethylhept-1-en-4-one Oxime

Prepared as in example 2; yield 1.00 g (6%)

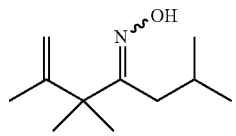

¹H NMR (400 MHz, CDCl₃): δ 0.84 (d, J=7.2 Hz, 6H), 1.19 (s, 6H), 1.58 (s, 3H), 2.05-2.17 (m, 3H), 4.80-4.81 (m, 2H).

Example 11

Synthesis of 2,3,3-trimethylnon-1-en-4-one

Prepared as in example 1; yield 69.2 g (38%).

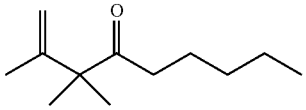

¹H NMR (400 MHz, CDCl₃): δ 0.80 (t, J=7.2 Hz, 3H), 1.15-1.25 (m, 10H), 1.40-1.48 (m, 2H), 1.56 (s, 3H), 2.32 (t, J=7.6 Hz, 2H), 4.87 (s, 2H); ¹³C NMR (100 MHz, CDCl₃): δ 14.0, 20.3, 22.6, 23.4, 23.9, 31.6, 36.4, 53.8, 111.7, 148.1, 214.0.

Example 12

Synthesis of 2,3,3-trimethylnon-1-en-4-one Oxime

Prepared as in example 2; yield 4.50 g (43%).

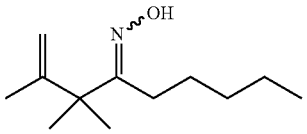

¹H NMR (400 MHz, CDCl₃): δ 0.95 (t, J=7.6 Hz, 3H), 1.30-1.34 (m, 10H), 1.51-1.60 (m, 2H), 1.67 (s, 3H), 2.14-2.18 (m, 2H), 4.91 (s, 2H), 9.69 (s, br. 1H); ¹³C NMR (100 MHz, CDCl₃): δ 13.9, 19.9, 22.7, 24.8, 25.4, 25.8, 32.6, 46.5, 110.6, 149.5, 165.0.

Example 13

Synthesis of 2,4,4,5-tetramethylhex-5-en-3-one

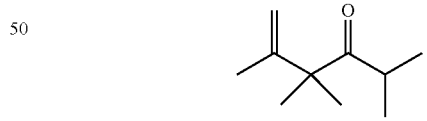

To a solution of 4,4,5-trimethylhex-5-en-3-one (45.0 g, 321 mmol) in tetrahydrofuran (1.80 L) potassium 2-methylpropan-2-olate (54.0 g, 481 mmol) was added at 0° C., over a period of 40 min under nitrogen atmosphere. The mixture was stirred between 0-5° C. for 30 min. Then iodomethane (49.9 mL, 802 mmol) was added dropwise and the mixture was allowed to warm to 20° C. and then stirred for 16 h. Subsequently, saturated aqueous NH₄Cl solution was added (200 mL) and the mixture extracted with ethyl acetate (2×200 mL). Combined organic fraction was dried over anhydrous Na₂SO₄ and volatiles were removed under reduced pressure. Crude product (65.6 g) was purified by fractional distillation using ss-packed column (39° C./3 mbar) to afford 2,4,4,5-tetramethylhex-5-en-3-one (36.2 g, 65.8%) as colorless liquid.

$^1$H NMR (600 MHz, CDCl$_3$): δ 1.00 (d, J=6.7 Hz, 6H), 1.25 (s, 6H), 1.66 (s, 3H), 3.03-3.11 (m, 1H), 5.00 (br. d, J=7.1 Hz, 1H).

$^{13}$C NMR (151 MHz, CDCl$_3$): δ 20.6, 20.8, 23.1, 34.0, 54.4, 112.3, 147.3, 218.2.

Example 14

Synthesis of (E)-2,4,4,5-tetramethylhex-5-en-3-one Oxime

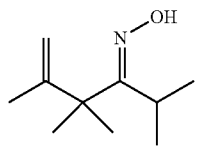

Mixture of pyridine (21.0 mL, 259 mmol), hydroxylamine hydrochloride (4.50 g, 64.8 mmol), 2,4,4,5-tetramethylhex-5-en-3-one (5.00 g, 32.4 mmol) and ethanol (20 ml) was stirred at 60° C. for 18 days. Then water (40.0 mL) and pentane (30 mL) were added. The organic fraction was separated and washed with water (2×20 mL) followed by brine (20 mL). Subsequently, volatiles were removed under reduced pressure and the residue purified by distillation in vacuo applying kugelrohr apparatus (90° C./7 mbar) to afford 2,4,4,5-tetramethylhex-5-en-3-one oxime (780 mg, 14%) as colorless crystals.

$^1$H NMR (600 MHz, DMSO) δ 10.26 (s, 1H), 4.92-4.89 (m, 1H), 4.88 (s, 1H), 2.32 (hept, J=7.0 Hz, 1H), 1.63 (s, 4H), 1.16 (s, 6H), 1.16 (d, J=7.0 Hz, 6H).

$^{13}$C NMR (151 MHz, DMSO) δ 163.39, 148.97, 111.04, 46.58, 28.58, 24.82, 19.69, 18.61.

Figure 2:
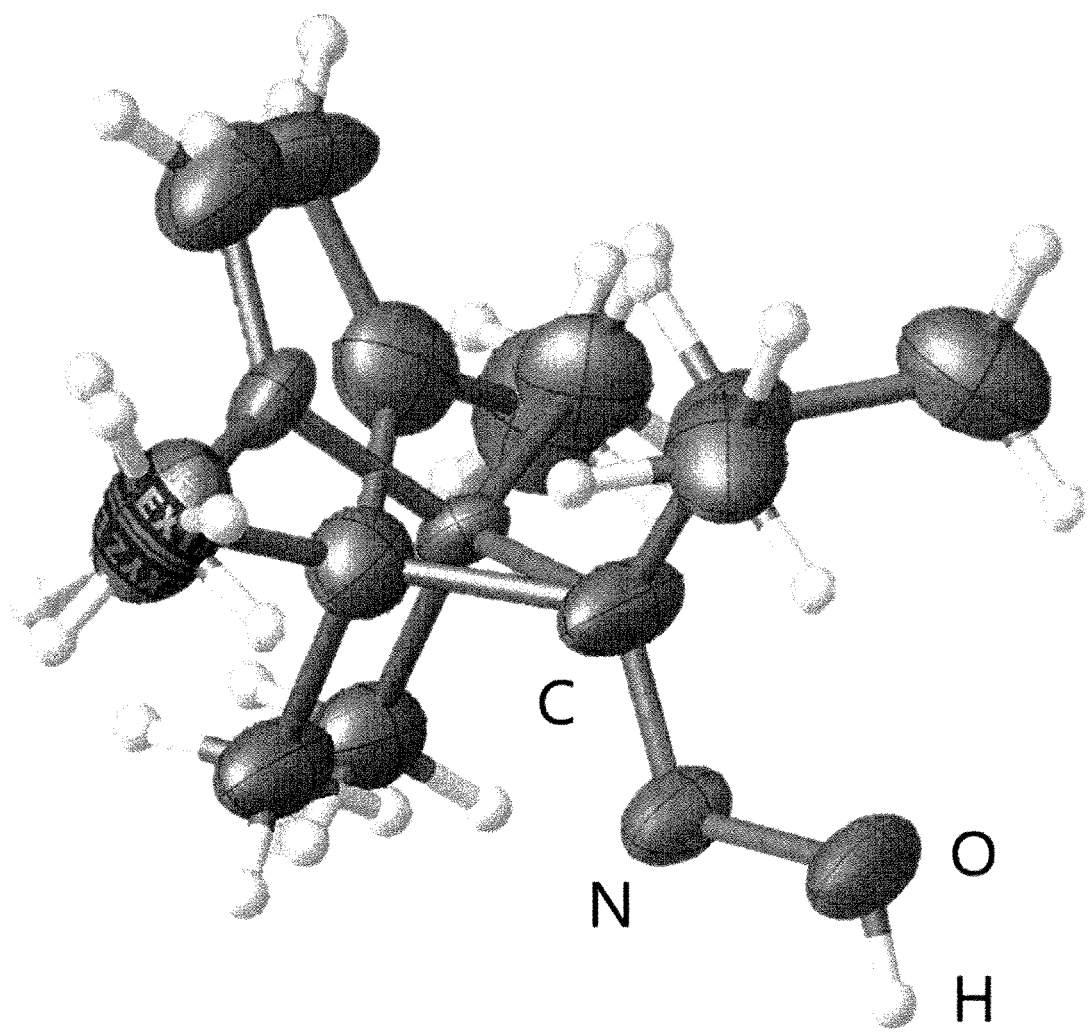
FIG. 2 illustrates a structure of the Z-2,4,4,5-tetramethylhex-5-en-3-one oxime molecule.

Recrystallization from pentane yielded crystals suitable for x-ray diffraction containing Z-2,4,4,5-tetramethylhex-5-en-3-one oxime molecule which crystallizes with 2 conformers within the crystal, sharing the same crystallographic site (see FIG. 2 which is appended at the end of the document):

Single crystal X-ray diffraction analysis: Empirical formula: C$_{10}$H$_{19}$NO; Formula weight: 169.26; Temperature/K: 173.00(10); Crystal system: monoclinic; Space group: P2$_1$/n; a/Å=7.7456(2); b/Å=11.0691(3); c/Å=12.8148(3); α/°=90; β/°=100.977(2); γ/°=90; Volume/Å$^3$=1078.60(5); Z=4; ρ$_{calc}$g/cm$^3$=1.042; μ/mm$^{-1}$=0.515; F(000)=376.0

Alternative Synthesis of 2,4,4,5-tetramethylhex-5-en-3-one Oxime

A solution of N,O-bis(trimethylsilyl)hydroxylamine (5.00 mL, 23.5 mmol) in THF (4.00 mL) was added to a suspension of potassium hydride (2.44 g, 21.3 mmol) in THF (10.0 mL) at −70° C. under nitrogen atmosphere. Then the suspension was warmed to 20° C. and stirred for 30 min. Subsequently, a solution of 2,4,4,5-tetramethylhex-5-en-3-one (3.28 g, 21.3 mmol) in THF (4 mL) was added at −70° C. The mixture was warmed to 20° C. and stirred for 18 h.

Subsequently, the mixture was poured to the mixture of ice and saturated aqueous ammonium chloride. The mixture was extracted twice with methyl tertbutyl ether.

The combined organic extract was washed with brine, dried over Na$_2$SO$_4$ and the volatiles were removed under reduced pressure. The residue was purified by distillation in vacuo applying kugelrohr apparatus (70-130° C./10 mbar) to afford 2,4,4,5-tetramethylhex-5-en-3-one oxime (1.91 g, 49%) as a pale-yellow solid.

Example 15

Synthesis of 3,3,4-trimethylpentan-2-one

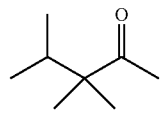

Raney Ni (20.0 mg, 340 μmop was added to a solution of 3,3,4-trimethylpent-4-en-2-one (2.50 g, 19.5 mmol) in iso-propanol (12 mL) at 25° C. and the reaction mixture was stirred under hydrogen atmosphere at 60° C./14 bar for 48 h. The reaction mixture was cooled to 25° C., filtered through a pad of celite and the solvent was removed under reduced pressure to afford 3,3,4-trimethylpentan-2-one (2.40 g, 94%).

Example 16

Synthesis of 2,3,3,6-trimethylhepta-1,5-dien-4-one

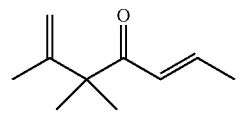

2,3-Dimethyl-1-butene (284 g, 405 mL, 3.38 mol) was added to a solution of trifluoromethanesulfonic acid (5.07 g, 3.0 mL, 33.8 mmol) in crotonic anhydride (521 g, 500 mL, 3.38 mol) at −20° C. under nitrogen atmosphere. Then the mixture was stirred at 0° C. for 30 min, and at 20° C. for 12 h. Subsequently, 2M sodium hydroxide solution (2.53 L, 5.07 mol) was added, the mixture was stirred at 50° C. for 4 hours under nitrogen atmosphere and cooled to 20° C. Then organic fraction was separated and the aqueous fraction was washed with methyl terbutyl ether. The combined organic fractions were washed with brine, and dried over Na$_2$SO$_4$ The volatiles were removed under reduced pressure and the residue distilled in vacuo (50-52° C./4 mbar) to afford 2,3,3,6-trimethylhepta-1,5-dien-4-one (142 g, 22% yield).

$^1$H NMR (600 MHz, CDCl$_3$) δ 6.95 (dq, J=13.9, 6.9 Hz, 1H), 6.45-6.31 (m, 1H), 4.98 (d, J=3.6 Hz, 2H), 1.85 (dd, J=6.9, 1.6 Hz, 3H), 1.64 (s, 3H), 1.23 (s, 6H).

$^{13}$C NMR (151 MHz, CDCl$_3$) δ 202.01, 148.05, 142.58, 126.23, 111.76, 52.36, 23.16, 20.26, 18.15.

Example 17

Synthesis of 2,3,3,6-tetramethylhepta-1,5-dien-4-one

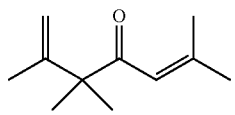

A mixture of titanium tetrachloride (15.8 g, 83.0 mmol) and tributylamine (17.1 g, 92.0 mmol) was added to a solution of 3,3,4-trimethylpent-4-en-2-one (10.0 g, 79.0 mmol) in dichloromethane (100 mL) at −60° C. under nitrogen atmosphere. Then the mixture was warmed to 20° C. and stirred for 30 min. Subsequently, acetone (4.70 g, 81.0 mmol) was added in one portion and the mixture was stirred for 1 h. Then the reaction mixture was cooled to −55° C. and pyridine (31.3 g, 396 mmol) was added and the mixture was left to reach 20° C.

The pale brown suspension was filtered over decalite and paper and the filtrate was purified by flash chromatography on silicagel with cyclohexane/methyl terbutyl ether mixture as eluent. The product was distilled in vacuo applying kugelrohr apparatus (110° C./7 mbar) to afford 2,3,3,6-tetramethylhepta-1,5-dien-4-one (3.50 g, 26%) as colorless oil.

$^1$H NMR (500 MHz, CDCl$_3$) δ 6.24-6.15 (m, 1H), 4.94 (dd, J=7.8, 6.5 Hz, 2H), 2.13 (d, J=1.0 Hz, 3H), 1.87 (d, J=1.0 Hz, 3H), 1.65 (s, 3H), 1.22 (s, 6H).

$^{13}$C NMR (126 MHz, CDCl$_3$) δ 203.65, 155.75, 149.01, 148.86, 120.04, 111.02, 53.19, 27.82, 23.45, 20.72, 20.25.

Example 18

Synthesis of (E)-2,3,3-trimethyl-6-phenylhepta-1,5-dien-4-one

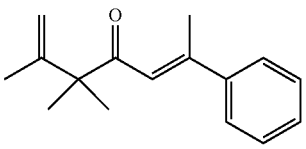 [SMILES: C=C(C)C(C)(C)C(=O)/C=C(\C)c1ccccc1]

A mixture of titanium tetrachloride (15.8 g, 83.0 mmol) and tributylamine (17.1 g, 92.0 mmol) was added to a solution of 3,3,4-trimethylpent-4-en-2-one (10.0 g, 79.0 mmol) in dichloromethane (100 mL) at −60° C. under nitrogen atmosphere. Then the mixture was warmed to 20° C. and stirred for 30 min. Subsequently, acetophenone (9.50 g, 79.0 mmol) added in one portion and the mixture was stirred for 1 h. Then the reaction mixture was cooled to −55° C. and pyridine (31.3 g, 396 mmol) was added and the mixture was left to reach 20° C. The crude material was filtered over paper, and the filtrate was purified by flash chromatography on silicagel with cyclohexane/methyl terbutyl ether mixture as eluent. The product was distilled in vacuo applying kugelrohr apparatus (150° C./6 mbar) to afford (E)-2,3,3-trimethyl-6-phenylhepta-1,5-dien-4-one (4.17 g, 21%)

$^1$H NMR (500 MHz, CDCl$_3$) δ 7.43 (dd, J=7.9, 1.8 Hz, 2H), 7.36 (dd, J=7.0, 0.8 Hz, 3H), 6.66 (d, J=1.3 Hz, 1H), 4.99 (dd, J=10.8, 9.5 Hz, 2H), 2.53 (d, J=1.3 Hz, 3H), 1.70 (s, 3H), 1.29 (s, 6H).

$^{13}$C NMR (126 MHz, CDCl$_3$) δ 204.13, 154.32, 148.74, 143.06, 128.90, 128.51, 126.52, 121.06, 111.44, 53.81, 23.53, 20.34, 18.42.

The olfactory properties of the compounds of formula (5-8) selected from above are given in the below table

| Compounds of formula (5-8) | IUPAC name | Olfactory notes |
| --- | --- | --- |
|  | 3,3,4-Trimethyl-pent-4-en-2-one | Camphoraceous, eucalyptus, piny |
|  | 4,4,5-Trimethyl-hex-5-en-3-one | Camphoraceous, piny |
|  | 2,4,4,5-tetramethylhex-5-en-3-one | Camphoraceous, slightly fruity, earthy |
|  | 2,3,3-Trimethyl-octa-1,7-dien-4-on | Thuja, coniferous, balsamic, dried fruity |

-continued

| Compounds of formula (5-8) | IUPAC name | Olfactory notes |
|---|---|---|
| | 2,4,4,5-tetramethylhexan-3-one | Earthy, camporaceous, minty, slightly foral-fruity |
| | 2,3,3-trimethylheptan-4-one | Floral, camphoraceous |
| | 2,3,3-Trimethyl-hepta-1,5-dien-4-one | Strong, diffusive, fruity, prune, armoise, artemisia, dried fruits, sultains, metallic |
| | 2,3,3,6-tetramethylhepta-1,5-dien-4-one | Dried fruits, plum, floral, camphoraceous, herbaceous, slightly earthy, woody, cooling effect |
| | 3,3,4-trimethylpentan-2-one oxime | Green, cassis, minty |
| | 4,4,5-trimethylhexan-3-one oxime | Cassis, fruity, peach skin, fresh, basil, green, isobutyl thiazole-like |
| | 2,3,3-trimethylheptan-4-one oxime | Cassis, peachy, stemmy, green |
| | 3,3,4-Trimethyl-pent-4-en-2-one oxime | Thyme, clary sage, cassis, eucalyptus |
| | 4,4,5-Trimethyl-hex-5-en-3-one oxime | Strong, herbel, green, basil, sage, catty |
| | 2,3,3-Trimethyl-hept-1-en-4-one oxime | Herbal, green, sage, fruity, cassis, lavender, natural |
| | 2,4,4,5-tetramethylhex-5-en-3-one oxime | Very powerful, cassis-catty, grapefruit, slightly earthy |

The disclosure is further illustrated by the following examples which in no way should be construed as being further limiting. One skilled in the art will readily appreciate that the specific methods and results described are merely illustrative.

COMPOSITIONS EXAMPLES

In the following invention examples (A/B/C) and comparative examples (D/E/F), the compounds of example S1, S2 and S3, and commercial compounds were included in a citrus accord fragrance for use in shampoo (G=blank). DPG=dipropylene glycol.

impression, almost catty and strongly enhances the overall strength of the fragrance at the same time (B).

The introduction of 0.005% by weight of 4,4,5-trimethylhex-5-en-3-one oxime provides this citrus accord with a distinct green character that with the citrus tends toward lime and enhances the overall strength of the fragrance at the same time (C).

Compared to three other oxime materials the following effects are observed:

Introduction of 0.005% by weight of Labienoxime gives a sharp, metallic top note effect (D).

Introduction of 0.005% by weight of Buccoxime gives a sharp, more green-harsh top note effect (E).

| Raw Materials (parts by weight) | Examples | | | | | | |
|---|---|---|---|---|---|---|---|
| | A | B | C | D | E | F | G |
| Aldehyde C10 | 40 | 40 | 40 | 40 | 40 | 40 | 40 |
| Citronellyl Nitrile | 64 | 64 | 64 | 64 | 64 | 64 | 64 |
| Damascone Delta 10% DPG | 15 | 15 | 15 | 15 | 15 | 15 | 15 |
| Ethyl Maltol | 2.5 | 2.5 | 2.5 | 2.5 | 2.5 | 2.5 | 2.5 |
| Litsea Cubeba Terpenes | 180 | 180 | 180 | 180 | 180 | 180 | 180 |
| Orange Oil Cold Pressed | 560 | 560 | 560 | 560 | 560 | 560 | 560 |
| PTBCA | 50 | 50 | 50 | 50 | 50 | 50 | 50 |
| Trans 2 Dodecenal | 2 | 2 | 2 | 2 | 2 | 2 | 2 |
| 2,4,4,5-tetramethylhex-5-en-3-one oxime 1% DPG | 5 | 0 | 0 | 0 | 0 | 0 | 0 |
| 4,4,5-trimethylhexan-3-one oxime 1% DPG | 0 | 5 | 0 | 0 | 0 | 0 | 0 |
| 4,4,5-trimethylhex-5-en-3-one oxime 1% DPG | 0 | 0 | 5 | 0 | 0 | 0 | 0 |
| Labienoxime 1% DPG | 0 | 0 | 0 | 5 | 0 | 0 | 0 |
| Buccoxime 1% DPG | 0 | 0 | 0 | 0 | 5 | 0 | 0 |
| Ribes Mercaptan 1% DPG | 0 | 0 | 0 | 0 | 0 | 5 | 0 |
| Dipropylene Glycol (DPG) | 81.5 | 81.5 | 81.5 | 81.5 | 81.5 | 81.5 | 86.5 |
| TOTAL | 1000 | 1000 | 1000 | 1000 | 1000 | 1000 | 1000 |

Comparative Studies of Different Compounds Where Column G is the Blank:

The introduction of 0.005% by weight of 2,4,4,5-tetramethylhex-5-en-3-one oxime provides this citrus accord with a natural juicy cassis/blackcurrant top note and enhances the overall strength of the fragrance at the same time (A).

The introduction of 0.005% by weight of 4,4,5-trimethylhexan-3-one oxime provides this citrus accord with a distinctly cassis-like top-end with an herbal/clary sage Introduction of 0.005% by weight of Ribes Mercaptan gives a more red-fruity aspect but not cassis (F).

In the following invention examples (A/B/C) and comparative examples (D/E/F), the compounds of example S1, S2 and S3, and commercial compounds were included in an Apple Accord Fragrance for use in shampoo (G=blank). DPG=dipropylene glycol.

| Raw Materials | A | B | C | D | E | F | G |
|---|---|---|---|---|---|---|---|
| Aldehyde C14 | 140 | 140 | 140 | 140 | 140 | 140 | 140 |
| Amyl Butyrate | 16 | 16 | 16 | 16 | 16 | 16 | 16 |
| Amyl Cinnamic Aldehyde | 65 | 65 | 65 | 65 | 65 | 65 | 65 |
| Triplal | 9 | 9 | 9 | 9 | 9 | 9 | 9 |
| Galaxolide 50 IPM | 235 | 235 | 235 | 235 | 235 | 235 | 235 |
| Hexyl Cinnamic Aldehyde | 85 | 85 | 85 | 85 | 85 | 85 | 85 |
| Verdox | 325 | 325 | 325 | 325 | 325 | 325 | 325 |
| Prenyl Acetate | 25 | 25 | 25 | 25 | 25 | 25 | 25 |
| 2,4,4,5-tetramethylhex-5-en-3-one oxime 1% DPG | 5 | 0 | 0 | 0 | 0 | 0 | 0 |
| 4,4,5-trimethylhexan-3-one oxime 1% DPG | 0 | 5 | 0 | 0 | 0 | 0 | 0 |
| 4,4,5-trimethylhex-5-en-3-one oxime 1% DPG | 0 | 0 | 5 | 0 | 0 | 0 | 0 |
| Labienoxime 1% DPG | 0 | 0 | 0 | 5 | 0 | 0 | 0 |
| Buccoxime 1% DPG | 0 | 0 | 0 | 0 | 5 | 0 | 0 |
| Ribes Mercaptan 1% DPG | 0 | 0 | 0 | 0 | 0 | 5 | 0 |
| Dipropylene Glycol | 95 | 95 | 95 | 95 | 95 | 95 | 100 |
| TOTAL | 1000 | 1000 | 1000 | 1000 | 1000 | 1000 | 1000 |

Comparative Studies of Different Compounds Where Column E is the Blank:

The introduction of 0.005% by weight of 2,4,4,5-tetramethylhex-5-en-3-one oxime provides this apple accord with a natural juicy cassis/blackcurrant top note and gives a more ripe-apple impression; enhances the overall strength of the fragrance at the same time (column A).

The introduction of 0.005% by weight of 4,4,5-trimethylhexan-3-one oxime provides this apple accord with a distinct top-end cassis-like with an herbal/sage impression, almost catty and enhances the overall strength of the fragrance at the same time. Not as pronounced as with Citrus, combines very well with Verdox (B).

The introduction of 0.005% by weight of 4,4,5-trimethylhex-5-en-3-one oxime reinforces this apple accord by a herbal character, and adds a green freshness to the composition. Enhances the overall strength of the fragrance at the same time (C).

Compared to 3 other compounds the following effects are observed:

Introduction of Labienoxime of 0.005% gives a sharp, metallic top note and reduced the overall apple impression (column B).

Introduction of Buccoxime of 0.005% gives a sharp and much more green top note like in unripe apples (column C).

Introduction of Ribes Mercaptan of 0.5% gives a more red-apple effect but reduces the juicy character (column D).

The invention claimed is:

1. A fragrance, flavor and/or deodorizing/masking composition comprising:
an oxime selected from compounds of formula (7) or of formula (8);

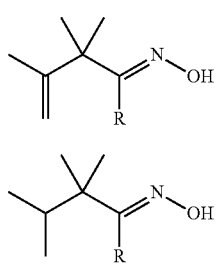

wherein R is an alkyl group having from 1 to 9 carbon atoms, an alkenyl group containing only one carbon-carbon double bond, said carbon-carbon double bond being optionally not conjugated with the oxime C=N bond, and having up to 9 carbon atoms, a substituted or unsubstituted aryl group having up to 8 carbon atoms, an oxo-alkyl group having up to 9 carbon atoms, or an alkoxyaryl group containing up to 9 carbon atoms or substituted or unsubstituted benzyl group having up to 9 carbon atoms,
wherein the fragrance, flavor and/or deodorizing/masking composition has at least one of a cassis, catty, tropical, green, coniferous, thuya, floral, and/or fruity olfactory note, and
wherein the compounds of formula (8) don't include those wherein R is phenyl.

2. The fragrance, flavor and/or deodorizing/masking compositions according to claim 1, wherein R is selected from the group consisting of methyl, ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 3-butenyl, 5-(2-methylpent-2-en)yl, 4-pent-2-enyl, 4-pent-1-enyl, 5-(2,5-dimethylhex-2-en)yl, benzyl, phenyl, and 4-methoxyphenyl, and wherein the compounds of formula (8) don't include those wherein R is phenyl.

3. The fragrance, flavor and/or deodorizing/masking compositions according to claim 1, wherein the oxime is selected from the group consisting of:

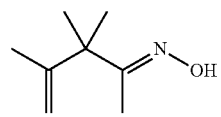
3,3,4-trimethylpent-4-en-2-one oxime;

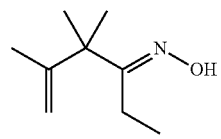
4,4,5-trimethylhex-5-en-3-one oxime;

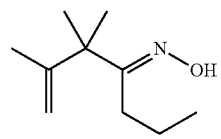
2,3,3-trimethylhept-1-en-4-one oxime;

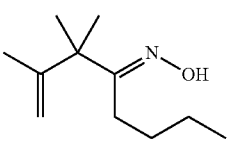
2,3,3-trimethyloct-1-en-4-one oxime;

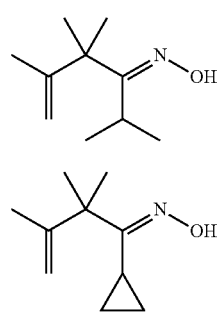
2,4,4,5-tetramethylhex-5-en-3-one oxime;

1-cyclopropyl-2,2,3-trimethylbut-3-en-1-one oxime;

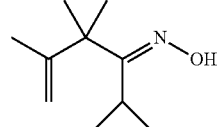
1-cyclobutyl-2,2,3-trimethylbut-3-en-1-one oxime;

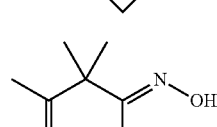
2,2,4,4,5-pentamethylhex-5-en-3-one oxime;

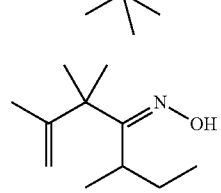
2,3,3,5-tetramethylhept-1-en-4-one oxime;

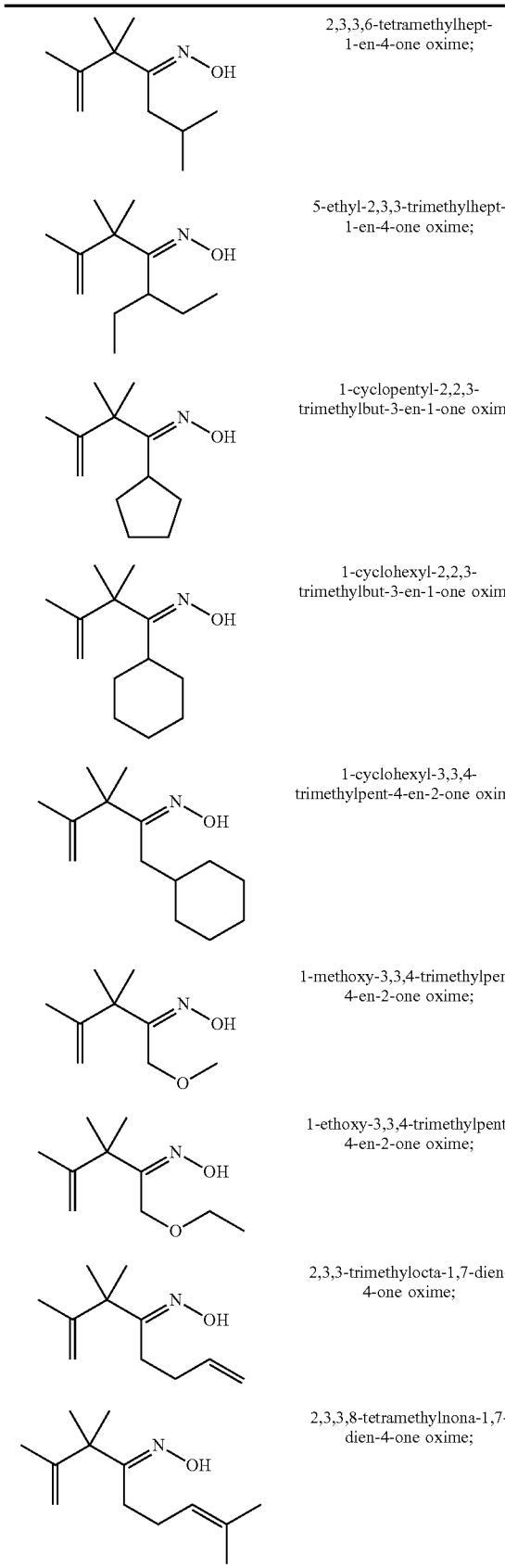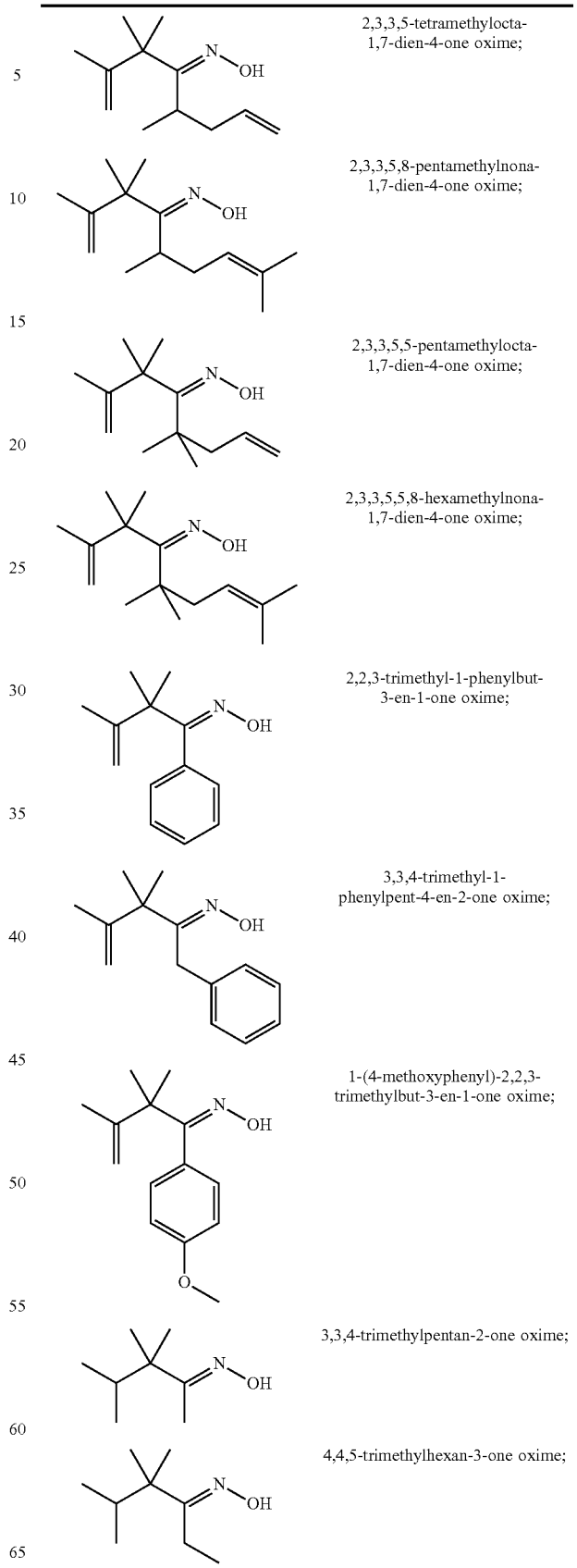

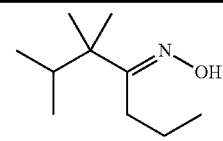 2,3,3-trimethylheptan-4-one oxime;

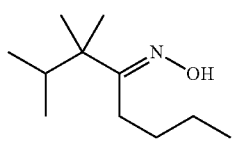 2,3,3-trimethyloctan-4-one oxime;

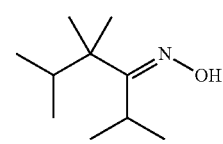 2,4,4,5-tetramethylhexan-3-one oxime;

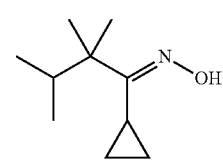 1-cyclopropyl-2,2,3-trimethylbutan-1-one oxime;

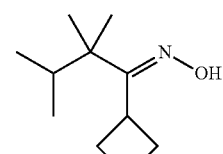 1-cyclobutyl-2,2,3-trimethylbutat-1-one oxime;

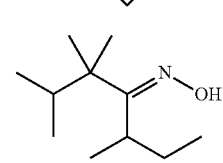 2,3,3,5-tetramethylheptan-4-one oxime;

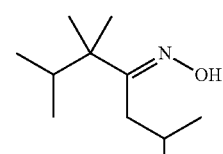 2,3,3,6-tetramethylheptan-4-one oxime;

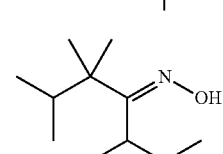 5-ethyl-2,3,3-trimethylheptan-4-one oxime;

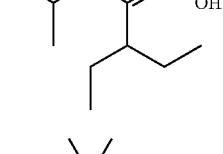 1-cyclopentyl-2,3,3-trimethylbutan-1-one oxime;

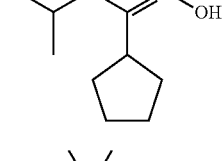 2,2,4,4,5-pentamethylhexan-3-one oxime;

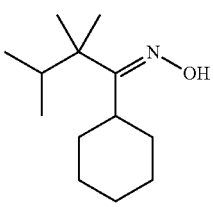 1-cyclohexyl-2,2,3-trimethylbutan-1-one oxime;

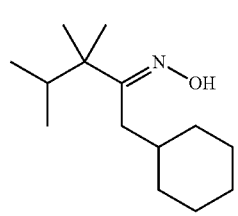 1-cyclohexyl-3,3,4-trimethylpentan-2-one oxime;

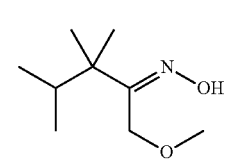 1-methoxy-3,3,4-trimethylpentan-2-one oxime;

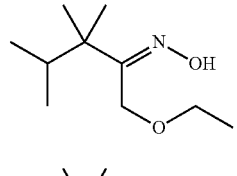 1-ethoxy-3,3,4-trimethylpentan-2-one oxime;

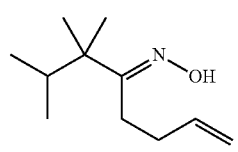 2,3,3-trimethyloct-7-en-4-one oxime;

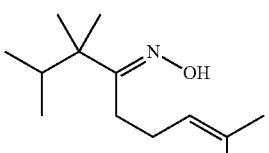 2,3,3,8-tetramethylnon-7-en-4-one oxime;

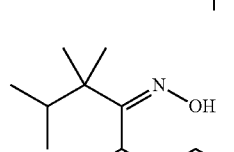 2,3,3,5-tetramethyloct-7-en-4-one oxime;

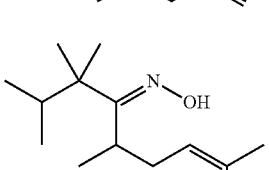 2,3,3,5,8-pentamethylnon-7-en-4-one oxime;

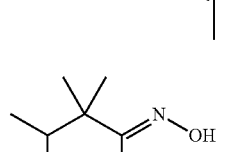 2,3,3,5,5-pentamethyloct-7-en-4-one oxime;

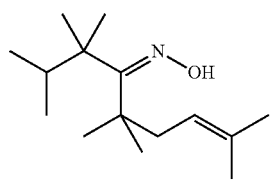 [SMILES: CC(C)=CCC(C)(C)/C(=N\O)C(C)(C)C(C)C]

2,3,3,5,5,8-hexamethylnon-7-en-4-one oxime; 5

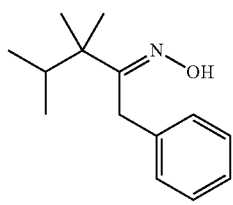 [SMILES: CC(C)C(C)(C)/C(Cc1ccccc1)=N/O]

3,3,4-trimethyl-1-phenylpentan-2-one oxime; 10

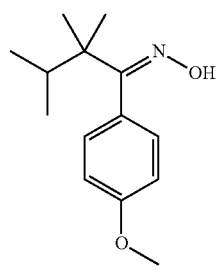 [SMILES: COc1ccc(/C(=N\O)C(C)(C)C(C)C)cc1]

1-(4-methoxyphenyl)-2,2,3-trimethylbutan-1-one oxime; 20 and a mixture of two or more of the said oximes.

4. The fragrance, flavor and/or deodorizing/masking compositions according to claim 1, wherein the content of the compounds of formula (7) and/or of formula (8) is comprised between 0.00001 and 99.9 wt %.

5. The fragrance, flavor and/or deodorizing/masking compositions according to claim 1, additionally comprising at least one ester and/or one alcohol.

6. The fragrance, flavor and/or deodorizing/masking compositions according to claim 5, wherein the total content of the compound(s) of formula (7) and/or of formula (8) together with the ester(s) and/or alcohol(s) is superior to 25 wt %.

7. The fragrance, flavor and/or deodorizing/masking compositions according to claim 6, wherein the total content of the compound(s) of formula (7) and/or of formula (8) together with the ester(s) and/or alcohols) is superior to 50 wt % superior to 75 wt %, or superior to 90 wt %.

8. The fragrance, flavor and/or deodorizing/masking compositions according to claim 1, comprising a mixture of oxime compounds according to formula (7) and/or formula (8) wherein the weight ratio between the oxime present in highest weight and the oxime present in the second highest weight in the mixture is comprised between 99.9% and 50%.

9. The fragrance, flavor and/or deodorizing/masking compositions according to claim 8, wherein the weight ratio between the oxime present in highest weight and the oxime present in the second highest weight in the mixture is comprised between 99% and 70%.

10. The fragrance, flavor and/or deodorizing/masking compositions according to claim 1, additionally comprising at least one ketone compound of formula (5) and/or (6)

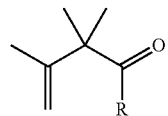

5

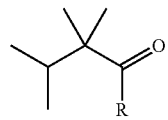

6 wherein R is an alkyl group having from 1 to 9 carbon atoms, an alkenyl group containing only one carbon-carbon double bond having up to 9 carbon atoms, a substituted or unsubstituted aryl group having up to 9 carbon atoms, an oxo-alkyl group having up to 9 carbon atoms, an alkoxyaryl group containing up to 9 carbon atoms or a substituted or unsubstituted benzyl group having up to 9 carbon atoms, and wherein the compounds of formula (8) don't include those wherein R is phenyl.

11. The fragrance, flavor and/or deodorizing/masking compositions according to claim 10, wherein the radical R of an oxime compound is identical to the radical R of a ketone compound.

12. The fragrance, flavor and/or deodorizing/masking compositions according to claim 10, wherein the weight ratio between the oxime(s) and the ketone(s) is comprised between 0.01% and 99.99%.

13. The fragrance, flavor and/or deodorizing/masking compositions according to claim 12, wherein the weight ratio between the oxime(s) and the ketone(s) is comprised between 80% and 99%.

14. A fragrance, flavor and/or deodorizing/masking composition according to claim 1 in a perfumed or flavored product.

15. An oxime useful in a fragrance, flavor and/or deodorizing/asking composition according to claim 1, wherein the oxime is selected from compounds of formula (7) or of formula (8):

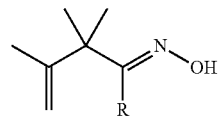

7

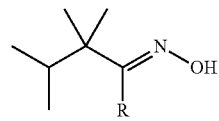

8 wherein R is an alkyl group having from 2 to 9 carbon atoms, alkenyl group containing only one carbon-carbon double bond, said carbon-carbon double bond being optionally not conjugated with the oxime C=N bond, and having up to 9 carbon atoms, a substituted or unsubstituted aryl group having up to 9 carbon atoms, an oxo-alkyl group having up to 9 carbon atoms, an alkoxyaryl group containing up to 9 carbon atoms or a substituted or unsubstituted benzyl group having up to 9 carbon atoms, and wherein the compounds of formula (8) don't include those wherein R is phenyl.

16. The oxime according to claim 15, wherein R is selected from the group consisting of ethyl, n-propyl, i-propyl, n-butyl, s-butyl, t-butyl, i-butyl, 2-pentyl, 3-pentyl, cyclopropyl, cyclobutyl, cyclopentyl, cyclohexyl, 1-(cyclohexylmethyl), (methoxy)methyl, (ethoxy)methyl, 3-butenyl, 5f2-methylpent-2-en)yl, 4-pent-2-enyl, 4 pent-1-enyl, 5-(2, 5-dimethylhex-2 en)yl, benzyl, phenyl, and 4-methoxyphenyl, and wherein the compounds of formula (8) don't include those wherein R is phenyl.

17. The oxime according to claim 15, wherein the oxime is selected from the group consisting of:

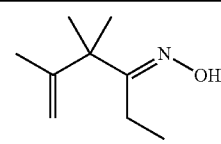
4,4,5-trimethylhex-5-en-3-one oxime;

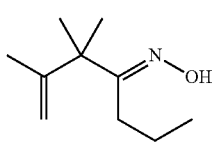
2,3,3-trimethylhept-1-en-4-one oxime;

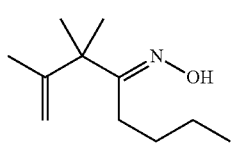
2,3,3-trimethyloct-1-en-4-one oxime;

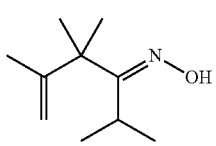
2,4,4,5-tetramethylhex-5-en-3-one oxime;

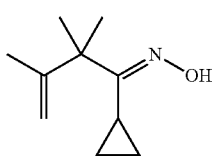
1-cyclopropyl-2,2,3-trimethylbut-3-en-1-one oxime;

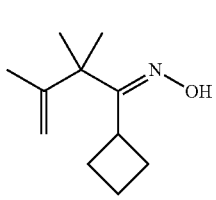
1-cyclobutyl-2,2,3-trimethylbut-3-en-1-one oxime;

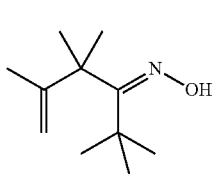
2,2,4,4,5-pentamethylhex-5-en-3-one oxime;

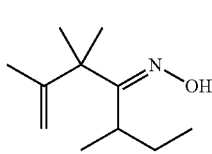
2,3,3,5-tetramethylhept-1-en-4-one oxime;

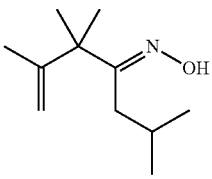
2,3,3,6-tetramethylhept-1-en-4-one oxime;

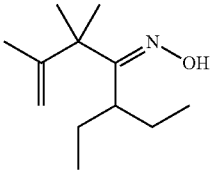
5-ethyl-2,3,3-trimethylhept-1-en-4-one oxime;

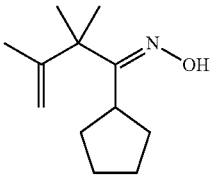
1-cyclopentyl-2,2,3-trimethylbut-3-en-1-one oxime;

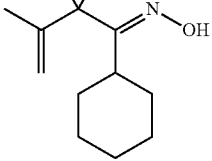
1-cyclohexyl-2,2,3-trimethylbut-3-en-1-one oxime;

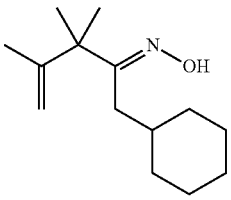 [SMILES: C=C(C)C(C)(C)/C(CC1CCCCC1)=N/O]
1-cyclohexyl-3,3,4-trimethylpent-4-en-2-one oxime;

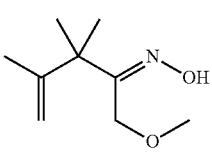
1-methoxy-3,3,4-trimethylpent-4-en-2-one oxime;

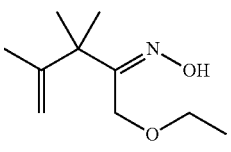
1-ethoxy-3,3,4-trimethylpent-4-en-2-one oxime;

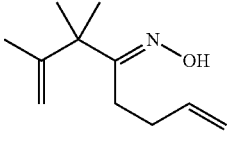
2,3,3-trimethylocta-1,7-dien-4-one oxime;

2,3,3,8-tetramethylnona-1,7-dien-4-one oxime;

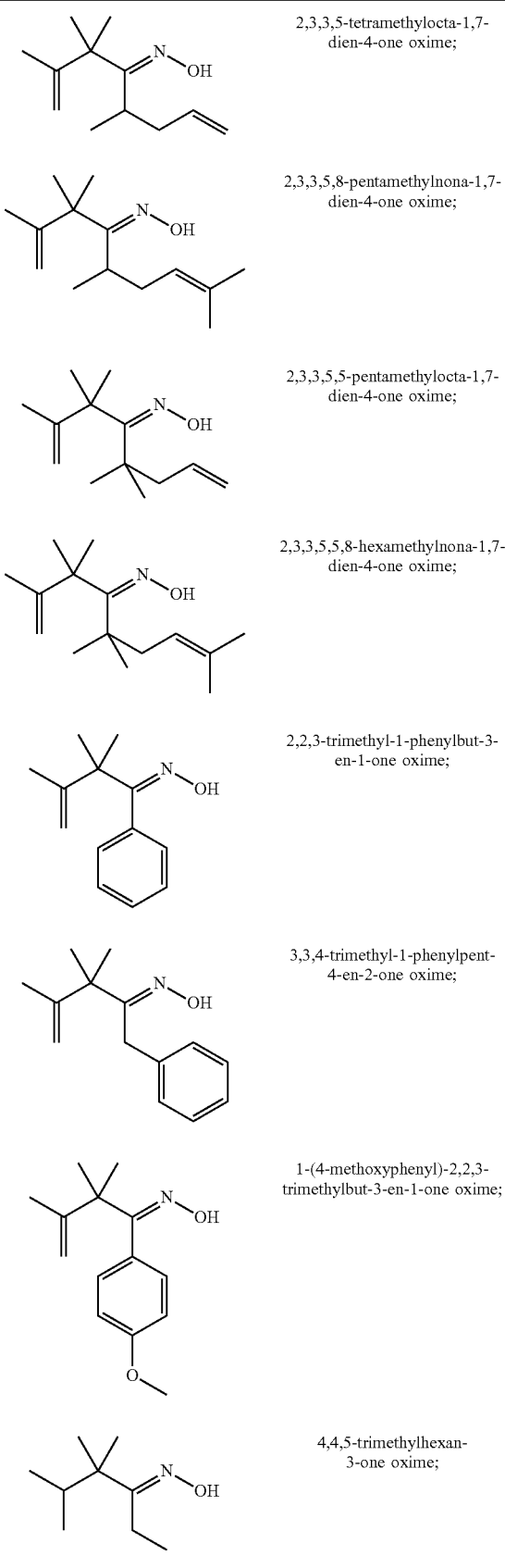
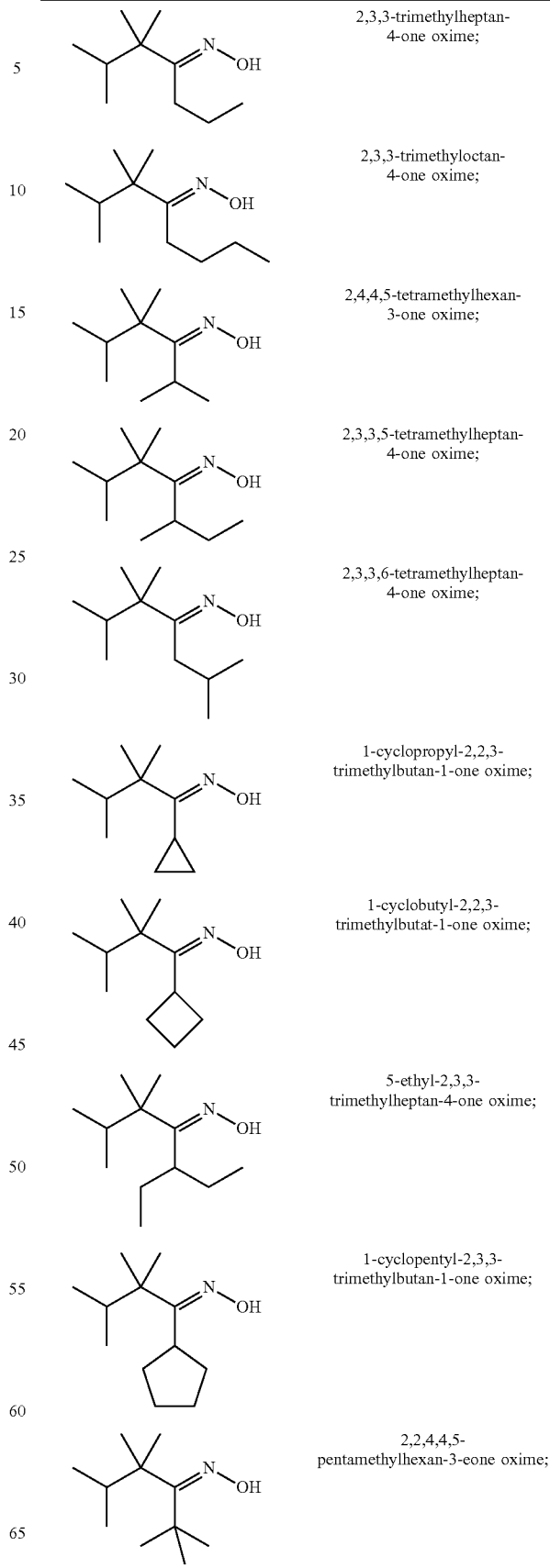

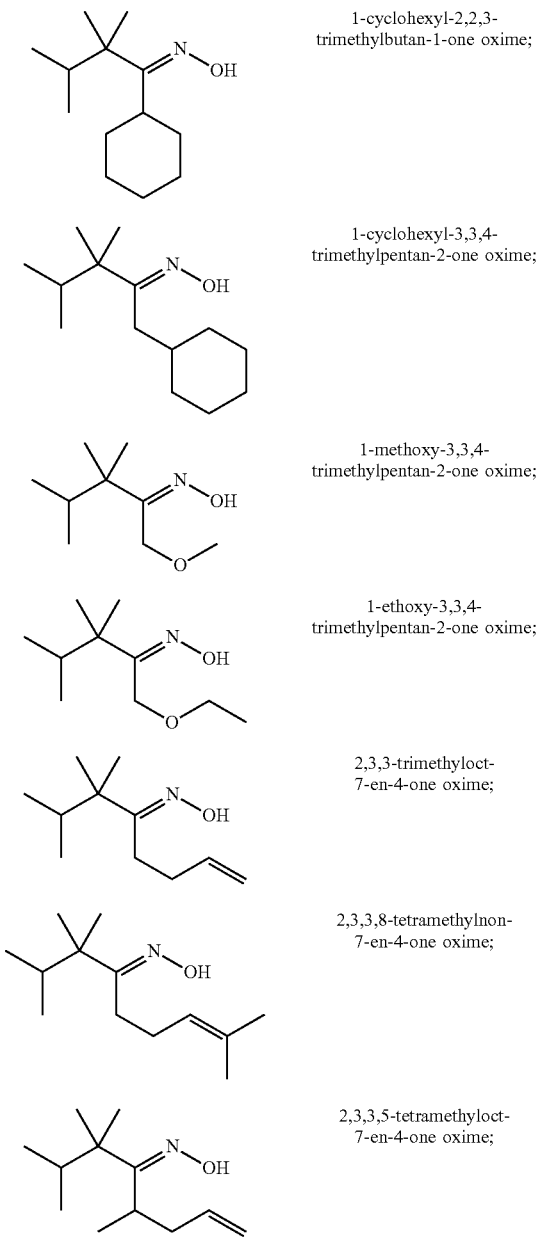
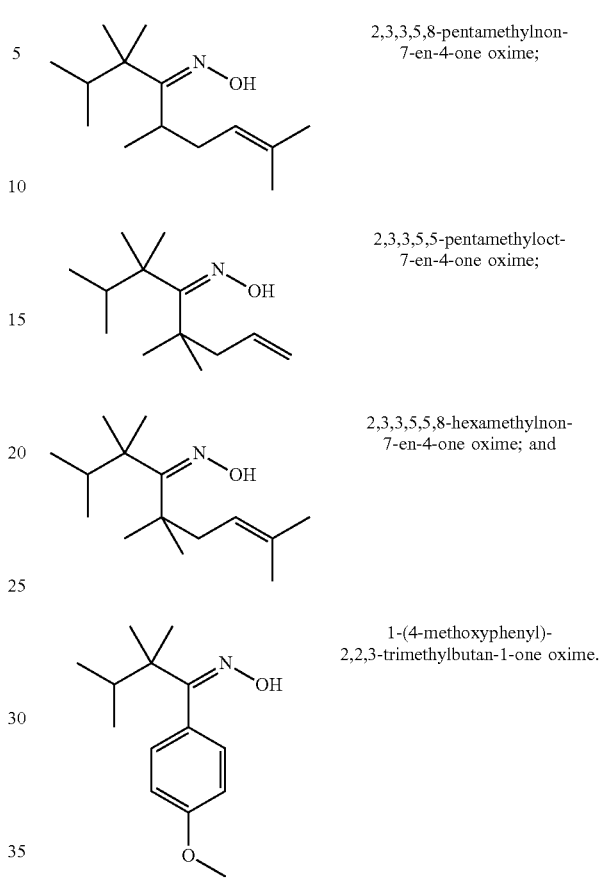

18. A mixture of oxime compounds according to claim 15, wherein the weight ratio between the oxime present in highest weight and the oxime present in the second highest weight in the mixture is comprised between 99.9% and 50%.

19. The mixture of oxime compounds according to claim 18, wherein the weight ratio between the oxime present in highest weight and the oxime present in the second highest weight in the mixture is comprised between 99% and 70%.

20. A oxime according to claim 15 in a perfumed or flavored product.

* * * * *